US006723736B2

(12) United States Patent
Dey et al.

(10) Patent No.: US 6,723,736 B2
(45) Date of Patent: Apr. 20, 2004

(54) TRICYCLIC COMPOUNDS AND USES THEREOF

(75) Inventors: Debendranath Dey, Fremont, CA (US); Partha Neogi, Fremont, CA (US); Ananda Sen, Castro Valley, CA (US); Somesh D. Sharma, Los Altos, CA (US); Bishwajit Nag, Fremont, CA (US)

(73) Assignee: Theracos, Inc., Sunnyvale, CA (US)

( * ) Notice: Subject to any disclaimer, the term of this patent is extended or adjusted under 35 U.S.C. 154(b) by 0 days.

(21) Appl. No.: 09/973,190

(22) Filed: Oct. 10, 2001

(65) Prior Publication Data

US 2002/0077333 A1 Jun. 20, 2002

Related U.S. Application Data

(60) Provisional application No. 60/238,475, filed on Oct. 10, 2000.

(51) Int. Cl.$^7$ .......................... A61K 31/34; A61K 31/47
(52) U.S. Cl. ........................ 514/305; 514/309; 546/141
(58) Field of Search .......................... 546/141; 514/305, 514/309

(56) References Cited

U.S. PATENT DOCUMENTS

| | | |
|---|---|---|
| 3,388,130 A | 6/1968 | Pesson |
| 3,457,266 A | 7/1969 | Gibas |
| 3,480,634 A | 11/1969 | Finkelstein |
| 3,629,265 A | 12/1971 | Grethe |
| 3,654,282 A | 4/1972 | Fourneau |
| 3,772,304 A | 11/1973 | Grethe |
| 3,872,130 A | 3/1975 | Kreighbaum |
| 3,910,927 A | 10/1975 | Kreighbaum |
| 3,954,771 A | 5/1976 | Geerts |
| 4,015,006 A | 3/1977 | Kreighbaum |
| 4,175,191 A | 11/1979 | Houlihan |
| 4,613,606 A | 9/1986 | Clark |
| 4,681,889 A | 7/1987 | Clark |
| 4,785,104 A | 11/1988 | Rabloczky |
| 4,801,593 A | 1/1989 | Hodson |
| 4,956,371 A | 9/1990 | Shoupe |
| 5,124,337 A | 6/1992 | Dugar |
| 5,272,270 A | 12/1993 | Hirsenkorn |
| 5,330,991 A | 7/1994 | Tokunaga |
| 5,401,752 A | 3/1995 | Tokunaga |
| 5,744,506 A | 4/1998 | Goldman |
| 6,031,106 A | 2/2000 | Harreus |

FOREIGN PATENT DOCUMENTS

| | | |
|---|---|---|
| EP | 0376197 A1 | 7/1990 |
| EP | 0376197 B1 | 10/1994 |
| JP | 57-163368 | 10/1982 |
| JP | 07-2785 | 1/1995 |
| WO | WO 96/38435 | 12/1996 |

OTHER PUBLICATIONS

Tellitu et al., "A Simple Enzymatic Synthesis of (3S,4R)–(+)– 4–Hydroxy–3–phenyltetrahydroisoquinolines" *Tetrahedron: Asymmetry*, 5:8(1994) 1567–1578.

Tellitu et al., "A Convenient Access to Protoberberine Derivatives" *Heterocyles*, 43:10 (1996) 2099–2112.

SanMartin et al., "3–Aryl–4–Isoquinolinone Derivatives an Efficient Oxidative Preparation" *Synthetic Communications*, 27:10 (1997) 1643–1652.

Badia et al., "Silicon–mediated Isoquinoline Synthesis: Preparation and Stereochemical Characterization of 4–Hydroxy–3–phenylisoquinolines" *Tetrahedron*, 48:21 (1992) 4419–4430.

SanMartin et al., "A New General Method for the Synthesis of 4–Hydroxylated 3–Aryltetrahydroisoquinolines" *Tetrahedron*, 51:18 (1995) 5361–5368.

Miura et al. "Synthesis, X–ray Analysis, and Acidolysis of exo– and endo–1–Methylindene Ozonides" *J. Am. Chem. Soc.* 105:8 (1983) 2414–2426.

Fujisaka et al. "Formation of Ethers from Ozonides by Reductive Cleavage of the Two C–O Bonds of the Peroxide Bridge" *J. Org. Chem.* 50:2 (1995) 275–277.

Normant–Chefnay, *Bull. Soc. Chim. Fr.*, No. 4 (1971) 1351–1362 (in French).

Normant–Chefnay, *Bull. Soc. Chim. Fr.*, No. 4 (1971) 1362–1371 (in French).

von Angerer et al., *Arch. Pharm.* 312:5 (1979) 385–389 (in German with English abstract).

Hori et al. "Stability of Thiabenzenes" *Chem. Pharm. Bull.* 22:10 (1974) 2485–2487.

Mulligan, Gail, *Dissertation Abstracts Int.* B 31:6 (1970) 3271–3272.

Hortmann et al. "Thiabenzenes. IV. Synthesis and Ylidic Properties of 1–Methyl–3,5–diphenylthiabenzene and 1–Aryl–2–methyl–2–thianaphthalenes" *J. Am. Chem. Soc.* 96:19 (1974) 6119–6132.

Crenshaw et al. "Potential Antifertility Agents. 1. Substituted Diaryl Derivatives of Benzo[b]thiophenes, Benzo[b]furans, 1H–2–Benzothiapyrans, and 2H–1–Benzothiapyrans" *J. Med. Chem.* 14:12 (1971) 1185–1190.

(List continued on next page.)

*Primary Examiner*—Amelia Owens
(74) *Attorney, Agent, or Firm*—Pillsbury Winthrop LLP

(57) ABSTRACT

Substituted isoquinolines, isochromanones and isothiochromanones that inhibit the pro-inflammatory cytokines tumor necrosis factor-alpha (TNF-alpha) and/or interleukin-6 (IL-6) and/or the enzyme cyclooxygenase-2 (COX-2) and/or interleukin-10 (IL-10). Compositions containing such compounds and methods of using such compounds for treatment and/or prevention of inflammation, inflammatory diseases, immunologic diseases and other diseases mediated by TNF-alpha, IL-6, COX-2 and/or IL-10 are also disclosed.

43 Claims, 7 Drawing Sheets

OTHER PUBLICATIONS

Abstract of Netherlands Patent Application (Written in Dutch): Robillard, Jean "Visible Phase Holograms" NL 740367 19740925, *Chemical Abstracts*, No. 88760v, vol. 83 (1975) p. 670.

Abstract of Symposium paper (written in English): Roensch, H. "Alpinigenine and cis–alpinigenine—stereochemical correlation and chemical degradations" IUPAC Int. Symp. Chem. Nat. Prod., vol. 2 (1978), *Chemical Abstracts*, No. 92:42186v, vol. 92 (1980) p. 808.

Carrillo et al. "Stereochemical studies on the synthesis of 1,2,3,4–tetrahydroisoquinolin–4–ols" *Tetrahedron: Asymmetry* 9 (1998) 1809–1816.

Gilchrist et al. "Reactive Intermediates. Part XXIV. 1H–Azirine Intermediates in the Pyrolysis of 1H–1,2, 3–Triazoles" *J. Chem. Soc. Perkin Trans.* 1:1 (1975) 1–8.

Howard Sard "An Unexpected Product During Synthesis of 3–Phenylisoquinoline: Improved Preparation of 4–Hydroxy–3–phenylisoquinoline" *J. Heterocyclic Chem.* 31 (1994) 1085–1087.

Whitney et al. "Isolation of a 1:1 Oxazole–Benzyne Cycloadduct: An Improved Method for Generating Benzyne and a New Approach to Isobenzofuran" *J. Org. Chem.* 53:23 (1988) 5595–5596.

Terent'ev et al. "Mass Spectrometry of 3–Substituted 4–Hydroxyisoquinolines and Their Derivatives" *Org. Mass Spectrom.* 11:3 (1976) 281–292.

Gilchrist et al. "Hydrogen Transfer in Iminocarbenes: a New Synthesis of Isoquinolines" *J. Chem. Soc. Commun.* 21 (1973) 835–836.

Pulima et al. "On the mechanism of the photochemical valence tautomerization of 2,3–diphenylindenome oxides" *J. Photochem. Photobiol.* 75:2 (1993) 143–150.

Padwa et al. "Photochemical Ring–Opening Reactions of Substituted Chromenes and Isochromenes" *J. Org. Chem.* 61:25 (1996) 9072.

Padwa et al. "Involvement of Enol Tautomers in the Photoisomerization of 3–Substituted Isochromanones" *J. Am. Chem. Soc.* 98:18 (1976) 5581–5590.

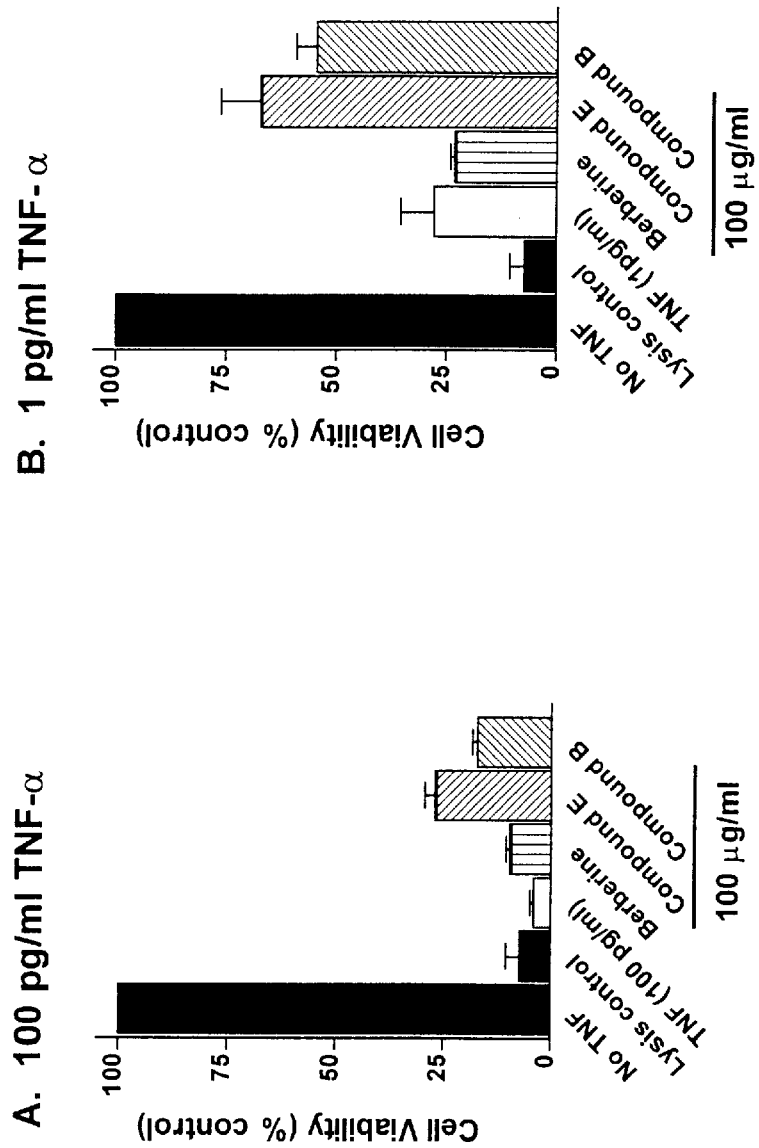
Figure 1. Inhibition of TNF-alpha Induced Cell Killing

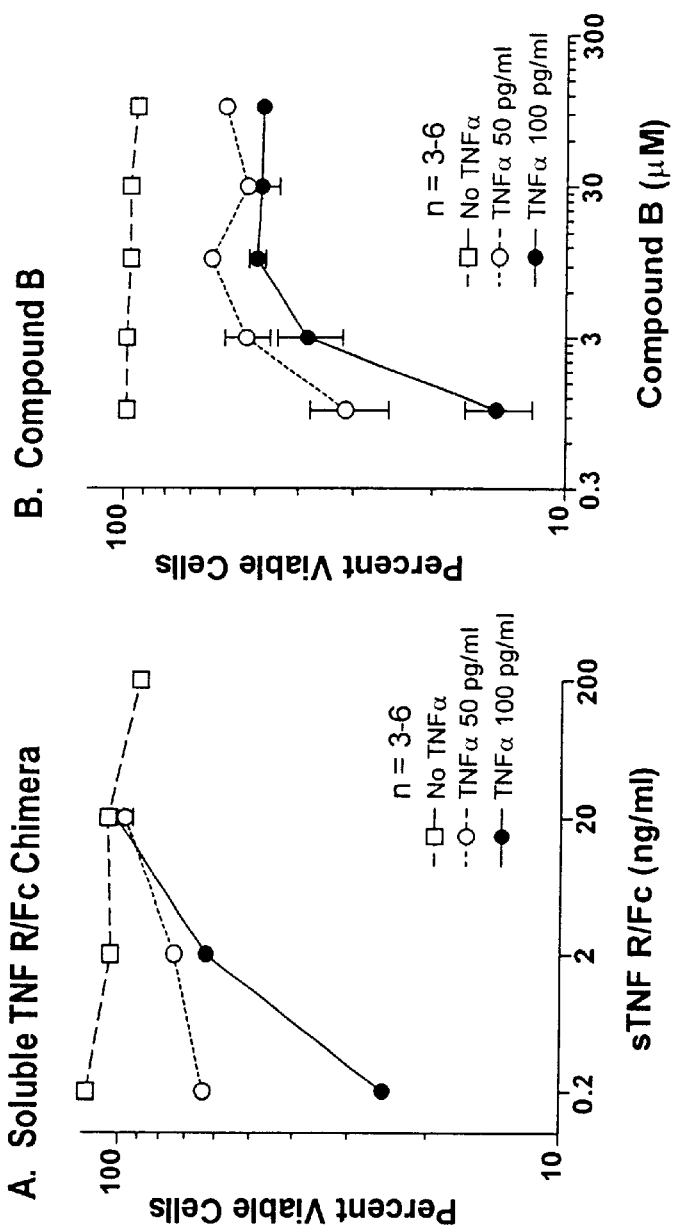
Figure 2. Dose Response of Inhibition of TNF-alpha Induced Cell Killing

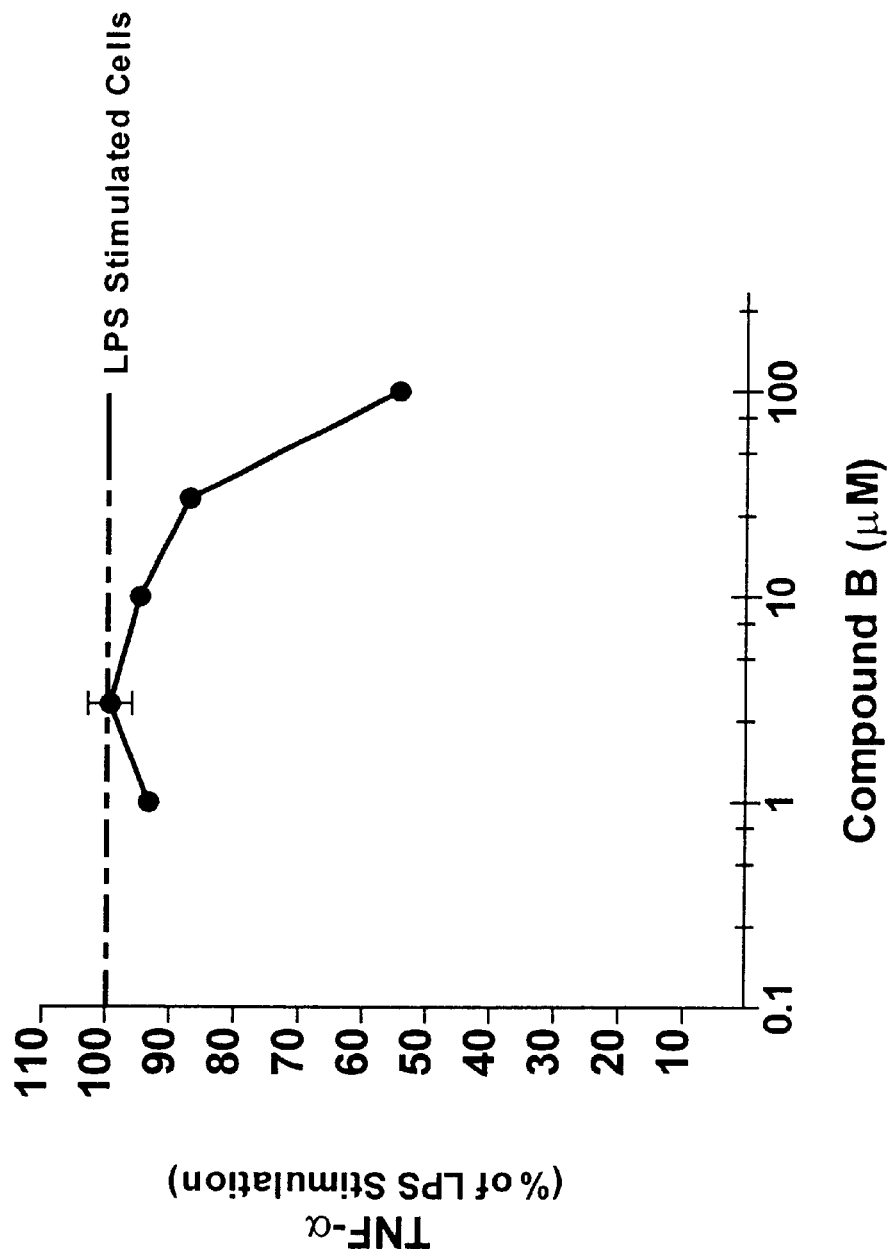
Figure 3. Inhibition of LPS-induced TNF-alpha Production

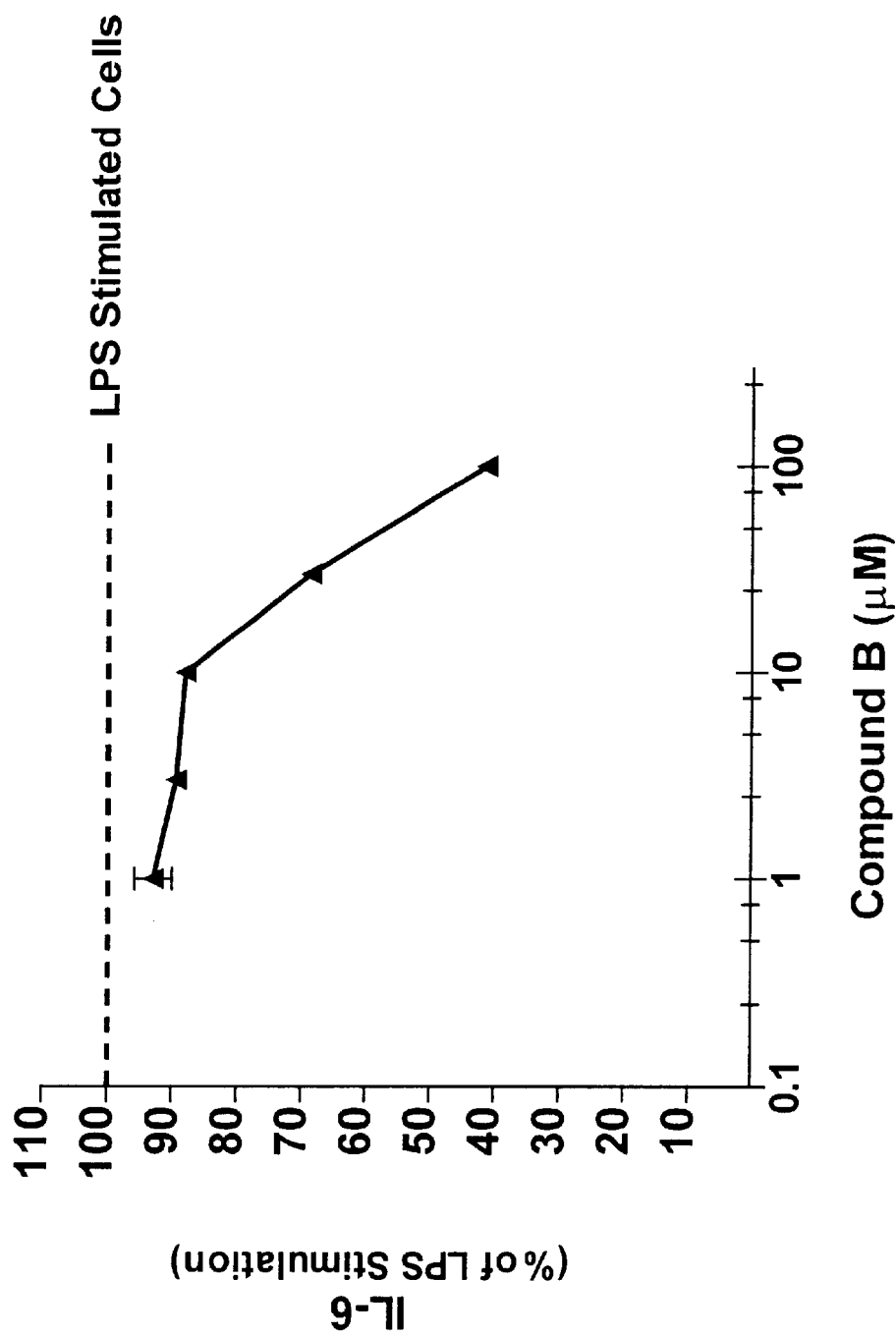

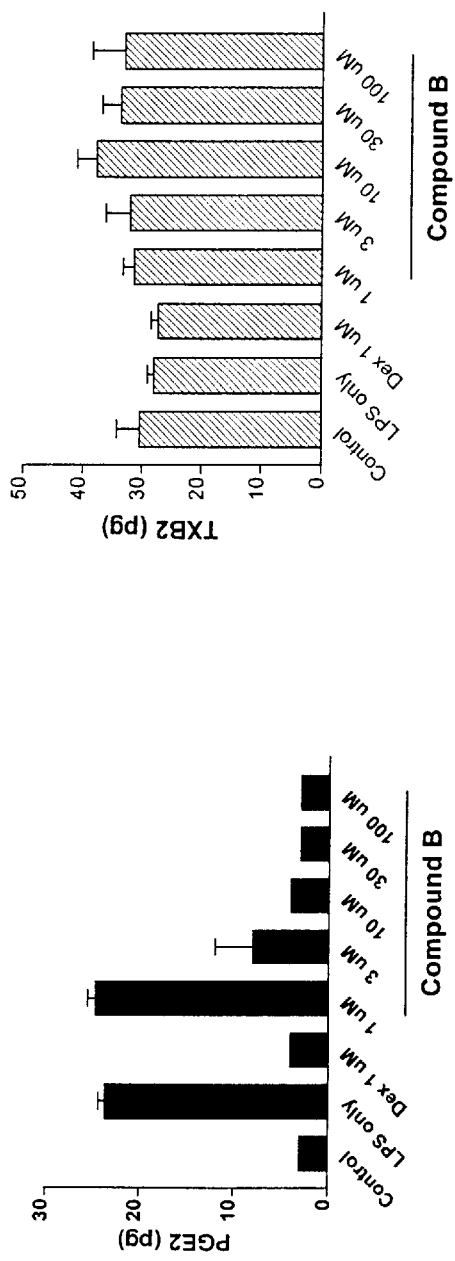
Figure 5. Selective Inhibition of LPS-induced COX-2 Activity

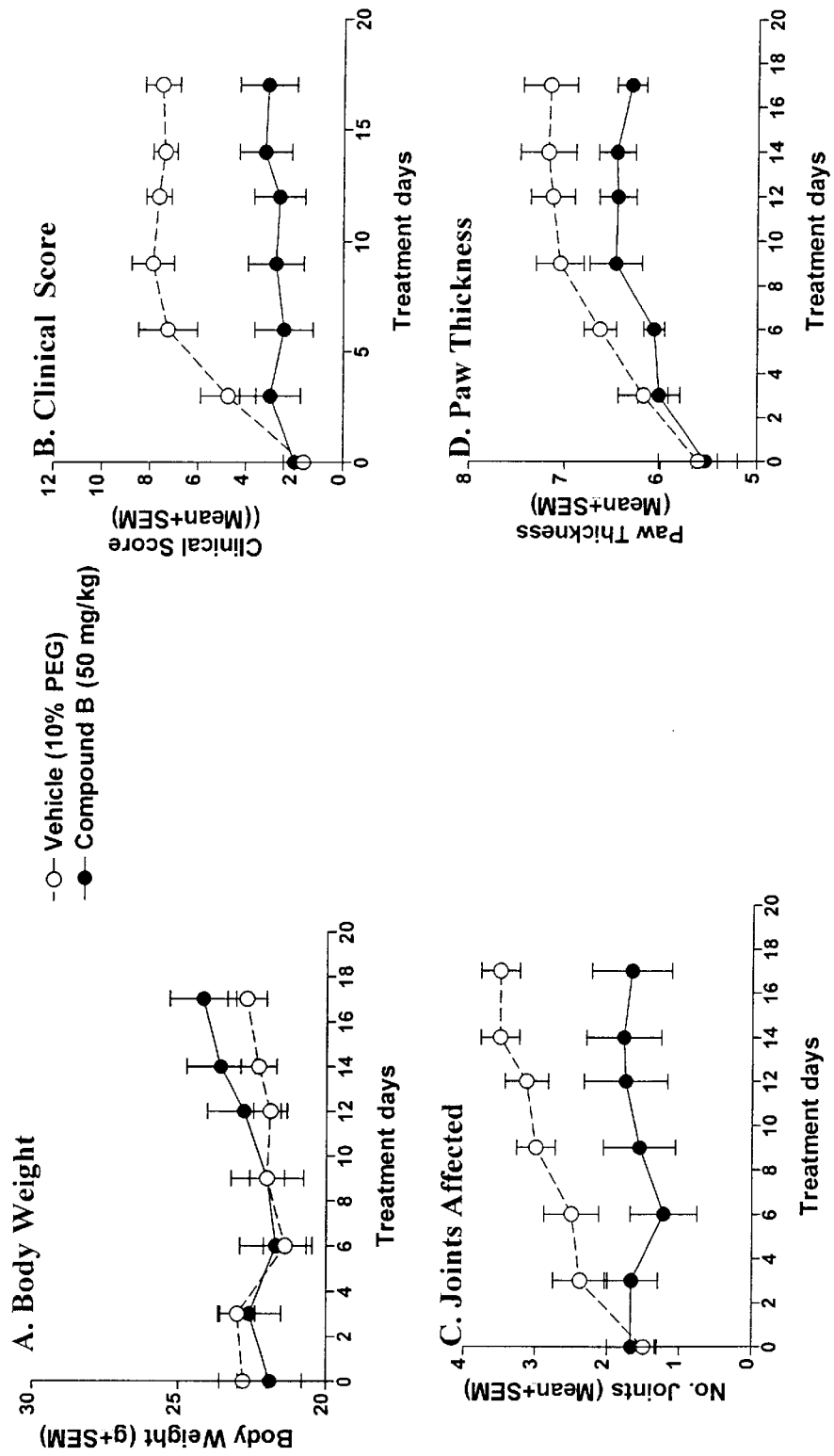
Figure 6. Suppression of Collagen-Induced Arthritis in Mice

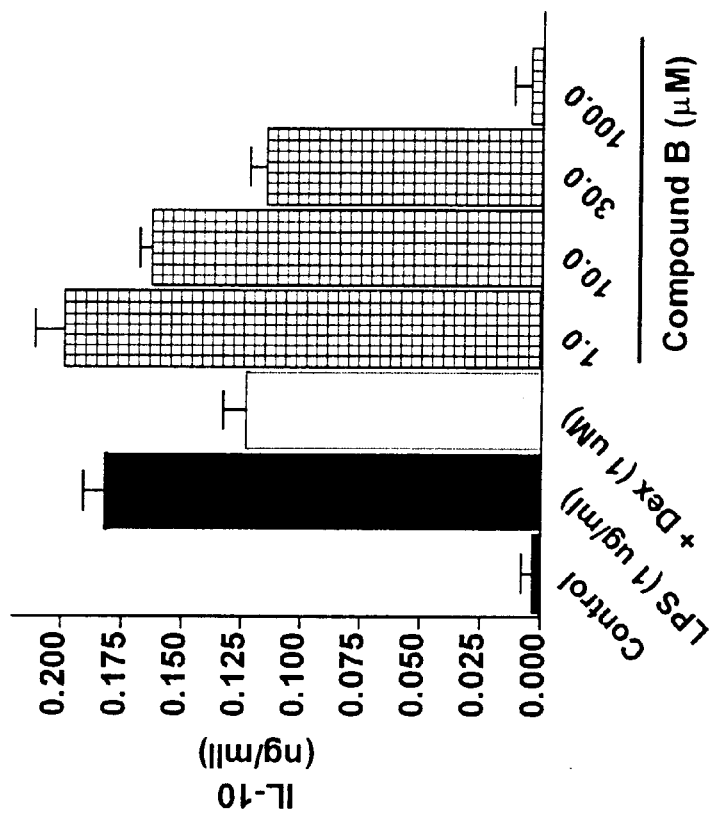
Figure 7. Inhibition of LPS-Induced IL-10 Production in PBMC

TRICYCLIC COMPOUNDS AND USES THEREOF

The present application is based on provisional application No. 60/238,475, filed Oct. 10, 2000, the contents of which are incorporated herein.

FIELD OF THE INVENTION

The present invention relates to tricyclic compounds, namely, substituted isoquinolines, isochromanones and isothiochromanones that inhibit the pro-inflammatory cytokines tumor necrosis factor-alpha (TNF-alpha) and/or interleukin-6 (IL-6) and/or the enzyme cyclooxygenase-2 (COX-2) and/or the cytokine interleukin-10 (IL-10). This invention also relates to compositions containing such compounds and methods using such compounds for treatment and/or prevention of inflammation, inflammatory diseases, immunologic diseases and other diseases mediated by TNF-alpha, IL-6, IL-10 and/or COX-2.

BACKGROUND OF THE INVENTION

The present invention is concerned with the modulation of cellular signaling pathways involving pro-inflammatory cytokines and cyclooxygenase-2 (COX-2). Cytokines are molecules secreted by immune cells that are important in mediating immune responses. Cytokine production may lead to the secretion of other cytokines, altered cellular function, cell division or differentiation. Inflammation is the body's normal response to injury or infection. However, in inflammatory diseases such as rheumatoid arthritis, pathologic inflammatory processes can lead to morbidity and mortality. The cytokine tumor necrosis factor-alpha (TNF-alpha) plays a central role in the inflammatory response and has been targeted as a point of intervention in inflammatory disease. TNF-alpha is a polypeptide hormone released by activated macrophages and other cells. At low concentrations, TNF-alpha participates in the protective inflammatory response by activating leukocytes and promoting their migration to extravascular sites of inflammation (Moser et al., *J Clin Invest*, 83:444–55, 1989). At higher concentrations, TNF-alpha can act as a potent pyrogen and induce the production of other pro-inflammatory cytokines (Haworth et al., *Eur J Immunol*, 21:2575–79, 1991; Brennan et al., *Lancet*, 2:244–7, 1989). TNF-alpha also stimulates the synthesis of acute-phase proteins. In rheumatoid arthritis, a chronic and progressive inflammatory disease affecting about 1% of the adult U.S. population, TNF-alpha mediates the cytokine cascade that leads to joint damage and destruction (Arend et al, *Arthritis Rheum*, 38:151–60, 1995). Inhibitors of TNF-alpha, including soluble TNF receptors (etanercept) (Goldenberg, *Clin Ther*, 21:75–87,1999) and anti-TNF-alpha antibody (infliximab) (Luong et al,*Ann Pharmacother*, 34:743–60, 2000), have recently been approved by the U.S. Food and Drug Administration (FDA) as agents for the treatment of rheumatoid arthritis.

Elevated levels of TNF-alpha have also been implicated in many other disorders and disease conditions, including cachexia (Fong et al., *Am J Physiol*, 256:R659–65, 1989), septic shock syndrome (Tracey et al, *Proc Soc Exp Biol Med*, 200:233–9, 1992), osteoarthritis (Venn et al., *Arthritis Rheum*, 36:819–26, 1993), inflammatory bowel disease such as Crohn's disease and ulcerative colitis (Murch et al., *Gut*, 32:913–7, 1991), Behcet's disease (Akoglu et al., *J Rheumatol*, 17:1107–8,1990), Kawasaki disease (Matsubara et al., *Clin Immunol Immunopathol*, 56:29–36, 1990), cerebral malaria (Grau et al.,*N Engl J Med*, 320:1586–91, 1989), adult respiratory distress syndrome (Millar et al., *Lancet*, 2:712–4, 1989), asbestosis and silicosis (Bissonnette et al., *Inflammation*, 13:329–39, 1989), pulmonary sarcoidosis (Baughman et al., *J Lab Clin Med*, 115:36–42, 1990), asthma (Shah et al., *Clin Exp Allergy*, 25:1038–44,1995), AIDS (Dezube et al., *J Acquir Immune Defic Syndr*, 5:1099–104, 1992), meningitis (Waage et al., *Lancet*, 1:355–7,1987), psoriasis (Oh et al., *J Am Acad Dermatol*, 42:829–30, 2000), graft versus host reaction (Nestel et al.,*J Exp Med*, 175:405–13, 1992), multiple sclerosis (Sharief et al., *N Engl J Med*, 325:467–72,1991), systemic lupus erythematosus (Maury et al., *Int J Tissue React*, 11:189=93, 1989), and diabetes (Hotamisligil et al., *Science*, 259:87–91, 1993).

It can be seen from the references cited above that inhibitors of TNF-alpha are potentially useful in the treatment of a wide variety of diseases. Compounds that inhibit TNF-alpha have been described in U.S. Pat. Nos. 6,090,763; 6,080,580; 6,075,041; 6,057,369; 6,048,841; 6,046,319; 6,046,221; 6,040,329; 6,034,100; 6,028,086; 6,022,884; 6,015,558; 6,004,974; 5,990,119; 5,981,701; 5,977,122; 5,972,936; 5,968,945; 5,962,478; 5,958,953; 5,958,409; 5,955,480; 5,948,786; 5,935,978; 5,935,977; 5,929,117; 5,925,636; 5,900,430; 5,900,417; 5,891,883; 5,869,677 and others.

Interleukin-6 (IL-6) is another pro-inflammatory cytokine that exhibits pleiotropy and redundancy of action. IL-6 participates in the immune response, inflammation and hematopoiesis. It is a potent inducer of the hepatic acute phase response and is a powerful stimulator of the hypothalamic-pituitary-adrenal axis that is under negative control by glucocorticoids. IL-6 promotes the secretion of growth hormone but inhibits release of thyroid stimulating hormone. Elevated levels of IL-6 are seen in several inflammatory diseases, and inhibition of the IL-6 cytokine subfamily has been suggested as a strategy to improve therapy for rheumatoid arthritis (Carroll et al., *Inflamm Res*, 47:1–7, 1998). In addition, IL-6 has been implicated in the progression of atherosclerosis and the pathogenesis of coronary heart disease (Yudkin et al., *Atherosclerosis*, 148:209–14, 1999). Overproduction of IL-6 is also seen in steroid withdrawal syndrome, conditions related to deregulated vasopressin secretion, and osteoporosis associated with increased bone resorption, such as in cases of hyperparathyroidism and sex-steroid deficiency (Papanicolaou et al., *Ann Intern Med*, 128:127–37, 1998).

Since excessive production of IL-6 is implicated in several disease states, it is highly desirable to develop compounds that inhibit IL-6 secretion. Compounds that inhibit IL-6 have been described in U.S. Pat. Nos. 6,004,813; 5,527,546 and 5,166,137.

Cyclooxygenase is an enzyme that catalyzes a rate-determining step in the biosynthesis of prostaglandins, which are important mediators of inflammation and pain. The enzyme occurs as at least two distinct isomers, cyclooxygenase-1 (COX-1) and cyclooxygenase-2 (COX-2). The COX-1 isomer is constitutively expressed in the gastric mucosa, platelets and other cells and is involved in the maintenance of homeostasis in mammals, including protecting the integrity of the digestive tract. The COX-2 isomer, on the other hand, is not constitutively expressed but rather is induced by various agents, such as cytokines, mitogens, hormones and growth factors. In particular, COX-2 is induced during the inflammatory response (DeWitt DL, *Biochim Biophys Acta*, 1083:121–34, 1991; Seibert et al., *Receptor*, 4:17–23, 1994). Aspirin and other conventional non-steroid anti-inflammatory drugs (NSAIDs) are non-selective inhibitors of both COX-1 and COX-2. They can be effective in reducing inflammatory pain and swelling, but since they hamper the protective action of COX-1, they produce undesirable side effects of gastrointestinal pathology. Therefore, agents that selectively inhibit COX-2 but not COX-1 are preferable for treatment of inflammatory diseases. Recently, a diarylpyrazole sulfonamide (celecoxib) that specifically blocks COX-2 has been approved by the FDA for use in the treatment of rheumatoid arthritis (Luong et al., *Ann Pharmacother,* 34:743–60, 2000; Penning et al., *J Med Chem,* 40:1347–65, 1997). COX-2 is also expressed in many cancers and precancerous lesions, and there is mounting evidence that selective COX-2 inhibitors may be useful for treating and preventing colorectal and other cancers (Taketo MM, *J Natl Cancer Inst,* 90:1609–20, 1998; Fournier et al., *J Cell Biochem Suppl,* 34:97–102, 2000). In 1999, celecoxib was approved by the FDA as an adjunct to usual care for patients with familial adenomatous polyposis, a condition which, left untreated, generally leads to colorectal cancer.

Compounds that selectively inhibit COX-2 have been described in U.S. Pat. Nos. 5,344,991; 5,380,738; 5,434,178; 5,466,823; 5,474,995; 5,510,368; 5,521,207; 5,521,213; 5,536,752; 5,550,142; 5,552,422; 5,604,260; 5,639,780; 5,643,933; 5,677,318; 5,691,374; 5,698,584; 5,710,140; 5,733,909; 5,789,413; 5,811,425; 5,817,700; 5,849,943; 5,859,257; 5,861,419; 5,905,089; 5,922,742; 5,925,631; 5,932,598; 5,945,539; 5,968,958; 5,981,576; 5,994,379; 5,994,381; 6,001,843; 6,002,014; 6,004,950; 6,004,960; 6,005,000; 6,020,343; 6,034,256; 6,046,191; 6,046,217; 6,057,319; 6,071,936; 6,071,954; 6,077,850; 6,077,868; 6,077,869 and 6,083,969.

The immunoregulatory cytokine interleukin-10 (IL-10) is a potent down-regulator of specific pro-inflammatory cytokines, but its role in inflammatory diseases and immune disorders is complex. Administration or overexpression of IL-10 is believed in many cases to counterbalance the action of pro-inflammatory cytokines and therefore to ameliorate inflammatory disease (Verhoef et al, *J Rheumatol,* 28:1960–6, 2001; McInnes et al, *J Immunol,* 167:4075–82, 2001; Lamblin et al, *J Allergy Clin Immunol,* 107:739–41, 2001; Cook et al, *Am Surg,* 67:237–41, 2001). In other cases, paradoxically, production or overexpression of IL-10 has been correlated with the promotion of inflammatory diseases or immune disorders, including systemic lupus erythematosus (Alarcon-Segovia, *Isr Med Assoc J,* 3:127–30, 2001; Bussolati et al, *Clin Exp Immunol* 122:471–6, 2000; Gonzalez-Amaro et al, *J Autoimmun,* 11:395–402,1998; Kalechman et al, *J Immunol,* 159:2658–67, 1997; Mongan et al, *Scand J Immunol* 46:406–12, 1997; Houssiau et al, *Lupus* 4:393–5, 1995), multiple sclerosis (Nakashima et al, *J Neuroimmunol,* 111:64–7, 2000; Navikas et al, *Scand J Immunol,* 41:171–8, 1995), myasthenia gravis (Ostlie et al, *J Immunol,* 166:4853–62, 2001; Huang et al, *Clin Exp Immunol,* 118:304–8,1999) and arthritis (Johansson et al, *J Immunol,* 167:3505–12, 2001).

Since elevated levels of IL-10 are associated with several disease states, compounds that inhibit IL-10 have potential therapeutic utility. Compositions and methods for inhibition of IL-10 have been described in U.S. Pat. Nos. 6,251,878; 6,239,260; 6,207,154; 6,184,372; 6,184,246 and 5,837,232.

It can be understood from the above discussions that a compound which inhibits both COX-2 and the pro-inflammatory cytokines TNF-alpha and IL-6 would be highly desirable for its potential use in treating diseases mediated by these agents, particularly inflammatory diseases such as rheumatoid arthritis and the like. It will also be apparent that compounds that inhibit IL-10 are desirable for their potential use in treating similar diseases, particularly autoimmune disorders.

Alkaloids such as sinomenine (Liu et al., *Int J Immunopharmacol,* 18:529–43, 1996), bukittinggine (Panthong et al., *Planta Med,* 64:530–5, 1998), tetrandine and berbamine (Wong et al., *Agents Actions,* 36:112–8, 1992) are well known for their anti-inflammatory activities. Isoquinoline derivatives with demonstrated or potential anti-inflammatory properties have also been described (van Muijlwijk-Koezen et al., *J Med Chem,* 43:2227–38, 2000; Xu et al., *J Nat Prod,* 62:1025–7, 1999; Chao et al., *J Med Chem,* 42:3860–73,1999; van Muijlwijk-Koezen et al., *J Med Chem,* 41:3987–93, 1998; van Muijlwijk-Koezen et al., *J Med Chem,* 41:3994–4000, 1998). Disease-modifying anti-rheumatic drugs (DMARDS) based on quinoline and related structures are also known (Baba et al., *Chem Pharm Bull [Tokyo],* 47:993–9,1999; Baba et al., *J Med Chem,* 39:5176–82, 1996). Berberine is an isoquinoline alkaloid that occurs naturally in plants belonging to the Berberidaceae and Ranunculaceae families. Extracts from these plants have been used for centuries in Eastern folk medicine as remedies for inflammation and hypertension. The anti-inflammatory effects of berberine and berberine-containing extracts have also been demonstrated in animal models (Ivanovska et al., *Int J Immunopharmacol,* 18:553–61, 1996; Yasukawa et al., *Chem Pharm Bull [Tokyo],* 39:1462–5,1991; Zhang et al., *Chung Kuo Yao Li Hsueh Pao,* 10:174–6,1989; Akhter et al., *Indian J Med Res,* 65:133–41, 1977) and in vitro studies (Ckless et al., *J Pharm Pharmacol,* 47:1029–31, 1995). The present invention describes novel substituted isoquinolines chemically distinct from, but having some structural features similar to, native berberine.

SUMMARY OF THE INVENTION

The present invention is directed to compounds that inhibit the production and/or activity of the pro-inflammatory cytokines tumor necrosis factor-alpha, interleukin-6, the enzyme cyclooxygenase-2 and/or interleukin-10, and therefore are useful for the prevention and/or treatment of inflammation, inflammatory diseases, immunologic diseases, autoimmune disorders and other diseases mediated by these agents. In particular, the subject invention discloses substituted isoquinolines of Formulas I–IV, isochromanones of Formulas V–VII, and isothiochromanones of Formulas VIII–X as well as the pharmaceutically acceptable salts and solvates thereof:

Formula I

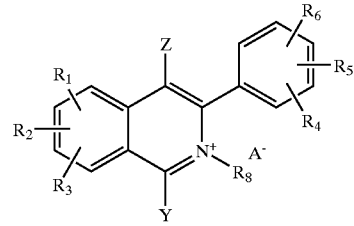

-continued

Formula II
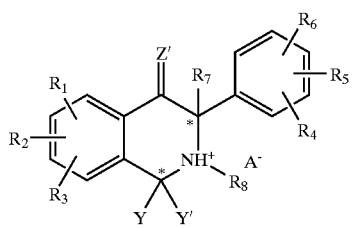

Formula III
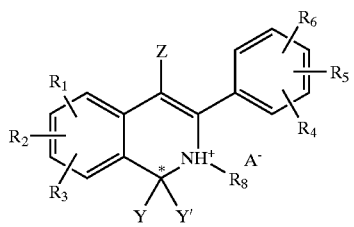

Formula IV
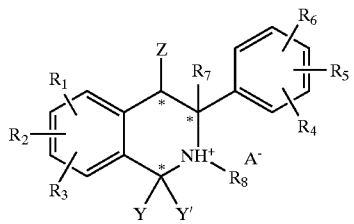

Formula V
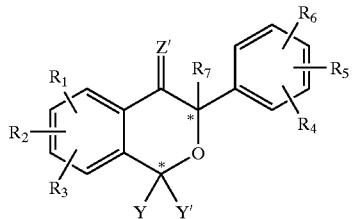

Formula VI
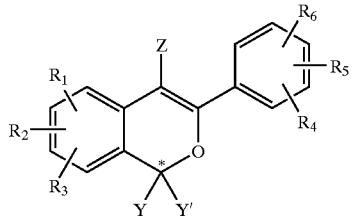

Formula VII
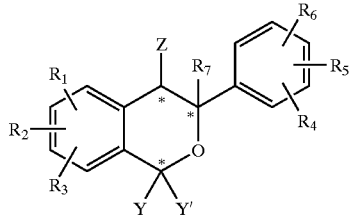

Formula VIII
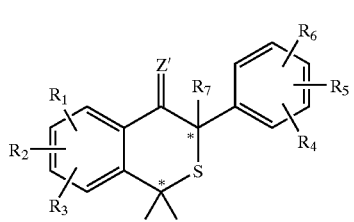

-continued

Formula IX
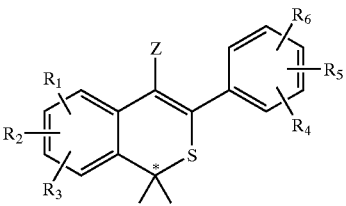

Formula X
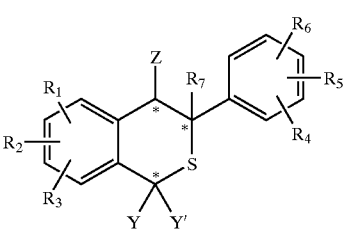

wherein the stereocenters marked with an asterisk (*) may be R— or S— and $R_1$, $R_2$, $R_3$, $R_4$, $R_5$ and $R_6$ are independently
H; optionally substituted $C_1$–$C_{20}$ linear or branched alkyl including chloroalkyl or fluoroalkyl; optionally substituted $C_2$–$C_{20}$ linear or branched alkenyl; optionally substituted $C_6$–$C_{20}$ aryl, linear or branched alkylaryl, linear or branched alkenylaryl; COOR where R is H, optionally substituted $C_1$–$C_{20}$ alkyl, optionally substituted $C_2$–$C_{20}$ alkenyl or optionally substituted $C_6$–$C_{10}$ aryl, sodium, potassium or other pharmaceutically acceptable counterion such as calcium, magnesium, ammonium, tromethamine and the like; CONR'R", where R' and R" are independently H, optionally substituted $C_1$–$C_{20}$ alkyl, optionally substituted $C_2$–$C_{20}$ alkenyl or optionally substituted $C_6$–$C_{10}$ aryl or where NR'R" represents a cyclic moiety such as morpholine, piperidine, piperazine and the like; $NH_2$; optionally substituted $C_1$–$C_{20}$ alkylamino, bis(alkylamino), cycloalkylamino or cyclic amino; OH; optionally substituted $C_1$–$C_{20}$ alkoxy, including trifluoromethoxy, and the like; optionally substituted $C_1$–$C_{20}$ alkanoyl; optionally substituted $C_1$–$C_{20}$ acyloxy; halo; optionally substituted $C_1$–$C_{20}$ alkylcarboxylamino; cyano; nitro; $SO_2NR'''R''''$ where R''' and R'''' are independently H, $C_1$–$C_{20}$ alkyl or aryl; $SO_2R'''$ where R''' is H, $C_1$–$C_{20}$ alkyl or aryl; $SO_3R'''$ where R''' is H, $C_1$–$C_{20}$ alkyl or aryl; or $C_4$–$C_8$ heterocycles such as tetrazolyl, imidazolyl, pyrrolyl, pyridyl, indolyl and the like; or when individual aromatic rings possess adjacent substituents, these substituents may be joined to form a ring such as a methylenedioxy or ethylenedioxy group, and the like, including lactones and lactams;

$R_7$ is
H (in which case the compounds may be in tautomeric form) or optionally substituted $C_1$–$C_{20}$ linear or branched alkyl including chloroalkyl or fluoroalkyl;

$R_8$ is
H; OH (or O in the case of Formula I); optionally substituted $C_1$–$C_{20}$ linear or branched alkyl including chloroalkyl or fluoroalkyl; optionally substituted $C_2$–$C_{20}$ linear or branched alkenyl; optionally substituted $C_6$–$C_{20}$ aryl, linear or branched alkylaryl, linear or branched alkenylaryl; COOR where R is H, optionally substituted $C_1$–$C_{20}$ alkyl, optionally substituted $C_2$–$C_{20}$ alkenyl or optionally substituted $C_6$–$C_{10}$ aryl, sodium, potassium or other pharmaceutically acceptable counter-ion such as calcium, magnesium, ammonium, tromethamine and the like; CONR'R", where R' and R" are independently H, optionally substituted $C_1$–$C_{20}$ alkyl, optionally substituted $C_2$–$C_{20}$ alkenyl or optionally substituted $C_6$–$C_{10}$ aryl or where NR'R" represents a cyclic moiety such as morpholine, piperidine, piperazine and the like; or optionally substituted alkanoyl, alkenoyl, aroyl, alkylaroyl or alkenylaroyl; and "$A^-$" represents a pharmaceutically acceptable counter-ion such as chloride, sulfate, phosphate, acetate and the like; or $R_8$ is absent, in which case the nitrogen does not bear a positive charge and the counter-ion "$A^-$" is not present;

Y and Y' are independently

H; optionally substituted $C_1$–$C_{20}$ linear or branched alkyl including chloroalkyl or fluoroalkyl; optionally substituted $C_2$–$C_{20}$ linear or branched alkenyl; optionally substituted $C_6$–$C_{20}$ aryl, linear or branched alkylaryl, linear or branched alkenylaryl; COOR where R is H, optionally substituted $C_1$–$C_{20}$ alkyl, optionally substituted $C_2$–$C_{20}$ alkenyl or optionally substituted $C_6$–$C_{10}$ aryl, sodium, potassium or other pharmaceutically acceptable counter-ion such as calcium, magnesium, ammonium, tromethamine and the like; CONR'R", where R' and R" are independently H, optionally substituted $C_1$–$C_{20}$ alkyl, optionally substituted $C_2$–$C_{20}$ alkenyl or optionally substituted $C_6$–$C_{10}$ aryl or where NR'R" represents a cyclic moiety such as morpholine, piperidine, piperazine and the like; $NH_2$; optionally substituted $C_1$–$C_{20}$ alkylamino, bis(alkylamino), cycloalkylamino or cyclic amino; OH; optionally substituted $C_1$–$C_{20}$ alkoxy, including trifluoromethoxy, and the like; optionally substituted $C_1$–$C_{20}$ alkanoyl; optionally substituted $C_1$–$C_{20}$ acyloxy; halo; optionally substituted $C_1$–$C_{20}$ alkylcarboxylamino; cyano; nitro; $SO_2NR'''R''''$ where R''' and R'''' are independently H, $C_1$–$C_{20}$ alkyl or aryl; $SO_2R'''$ where R''' is H, $C_1$–$C_{20}$ alkyl or aryl; $SO_3R'''$ where R''' is H, $C_1$–$C_{20}$ alkyl or aryl; or $C_4$–$C_8$ heterocycles such as tetrazolyl, imidazolyl, pyrrolyl, pyridyl, indolyl and the like; or Y and Y' together may be joined in a ring such as cyclopropyl, cyclobutyl, cyclopentyl, cyclohexyl and the like, including heterocycles such as lactones, lactams and the like;

Z is

OH; optionally substituted $C_1$–$C_{20}$ alkoxy, including trifluoromethoxy, and the like; NR'R", where R' and R" are independently H, optionally substituted $C_1$–$C_{20}$ alkyl, optionally substituted $C_2$–$C_{20}$ alkenyl or optionally substituted $C_6$–$C_{10}$ aryl or where NR'R" represents a cyclic moiety such as morpholine, piperidine, piperazine and the like; or SR'''' where R'''' is H, optionally substituted $C_1$–$C_{20}$ alkyl, optionally substituted $C_2$–$C_{20}$ alkenyl or optionally substituted $C_6$–$C_{10}$ aryl;

Z' is

O; S; or NR''''', where R''''' is H, optionally substituted $C_1$–$C_{20}$ alkyl, optionally substituted $C_2$–$C_{20}$ alkenyl or optionally substituted $C_6$–$C_{10}$ aryl;

with the provisos that in Formula I, when Y is H, then Z is OH, $R_8$ is H, and $R_1$, $R_2$ and $R_3$ are not 6-methoxy; when Y is methyl or substituted benzyl, then $R_1$, $R_2$ and $R_3$ do not comprise 6,7-dimethoxy or 5,6,7-trimethoxy or 6,7,8-trimethoxy; and when Z is OH, at least one of $R_1$, $R_2$, $R_3$, $R_4$, $R_5$ and $R_6$ is not H;

in Formula II, when Y is H and Y' is H, then Z' is O, $R_8$ is H, and $R_1$, $R_2$ and $R_3$ are not 6-methoxy;

when Y is H and Y' is methyl or substituted benzyl, then $R_1$, $R_2$ and $R_3$ do not comprise 6,7-dimethoxy or 5,6,7-trimethoxy or 6,7,8-trimethoxy; and when Z' is O, at least one of $R_1$, $R_2$, $R_3$, $R_4$, $R_5$, $R_6$ and $R_7$ is not H;

in Formula III, when Y is H and Y' is H, then Z is OH, $R_8$ is H, and $R_1$, $R_2$ and $R_3$ are not 6-methoxy;

when Y is H and Y' is methyl or substituted benzyl, then $R_1$, $R_2$ and $R_3$ do not comprise 6,7-dimethoxy or 5,6,7-trimethoxy or 6,7,8-trimethoxy; and when Z is OH or alkoxy, at least one of $R_1$, $R_2$, $R_3$, $R_4$, $R_5$ and $R_6$ is not H;

in Formula IV, when Y is H and Y' is H, then Z is OH, $R_8$ is H, and $R_1$, $R_2$ and $R_3$ are not 6-methoxy;

when Y is H and Y' is methyl or substituted benzyl, then $R_1$, $R_2$ and $R_3$ do not comprise 6,7-dimethoxy or 5,6,7-trimethoxy or 6,7,8-trimethoxy; and when Z is OH, at least one of $R_1$, $R_2$, $R_3$, $R_4$, $R_5$ and $R_6$ is not H;

in Formula V, when Z' is and Y and/or Y' is phenyl, then at least one of $R_1$, $R_2$, $R_3$, $R_4$, $R_5$ and $R_6$ is not H' when Z' is O and Y and/or Y' is alkoxy, then R, $R_5$ and $R_6$ are not aminoethyl; and when Z' is O and Y is H and Y' is H, then $R_1$ is not H;

in Formula VI, when Z is OH and Y and/or Y' is phenyl, then at least one of $R_1$, $R_2$, $R_3$, $R_4$, $R_5$ and $R_6$ is not H;

in Formula VII, when Z is methyl or phenyl, then at least one of $R_1$, $R_2$, $R_3$, $R_4$, $R_5$, $R_6$ and $R_7$ is not H;

when Z is OH and Y and/or Y' is phenyl, then at least one of $R_1$, $R_2$, $R_3$, $R_4$, $R_5$ and $R_6$ is not H;

when Z is OH and Y and/or Y' is alkoxy, then $R_4$, $R_5$ and $R_6$ are not aminoethyl; and when Z is OH and Y is H and Y' is H, then $R_7$ is not H;

in Formula VIII, when Y and/or Y' is substituted alkyl, arylamide or COOR, and $R_1$ and $R_2$ comprise 6,7-dimethyl or 5,6-dihydroxy, then at least one of $R_4$, $R_5$ and $R_6$ is not H; and when Z' is O, then at least one of $R_1$, $R_2$, $R_3$, $R_4$, $R_5$, $R_6$ and $R_7$ is not H, and $R_1$, $R_2$ and $R_3$ do not comprise 7-methoxy;

in Formula IX, when Y and/or Y' is substituted alkyl, arylamide or COOR, and $R_1$ and $R_2$ comprise 6,7-dimethyl or 5,6-dihydroxy, then at least one of $R_4$, $R_5$ and $R_6$ is not H; and when Z is OH or alkoxy, then at least one of $R_1$, $R_2$, $R_3$, $R_4$, $R_5$ and $R_6$ is not H, and $R_1$, $R_2$ and $R_3$ do not comprise 7-methoxy;

in Formula X, when Y is substituted alkyl, arylamide or COOR, and $R_1$ and $R_2$ comprise 6,7-dimethyl or 5,6-dihydroxy, then at least one of $R_4$, $R_5$ and $R_6$ is not H;

when Z is H, then at least one of Y, Y', $R_4$, $R_5$ and $R_6$ is not H; and when Z is OH, at least one of $R_1$, $R_2$, $R_3$, $R_4$, $R_5$, $R_6$ and $R_7$ is not H and provided further that Z may be H in the case of compounds of Formula IX or Formula X.

Another aspect of the present invention relates to pharmaceutical compositions containing the compounds of Formulas I to X, which compositions are suitable for administration to animals, more preferably mammals, and most preferably humans.

In another aspect of the present invention, methods are disclosed for using the compounds of Formulas I to X for the treatment and/or prevention of inflammation, inflammatory diseases, immunologic diseases and other diseases mediated by TNF-alpha, IL-6, COX-2 and/or interleukin-10 (IL-10).

BRIEF DESCRIPTION OF THE DRAWINGS

FIG. 1 shows the ability of compounds B and E, representing compounds according to Formulas I and II, respectively, to inhibit TNF-alpha activity in an in vitro assay for TNF-alpha induced cell killing;

FIG. 2 shows the dose response of the ability of compound B to inhibit TNF-alpha activity in an in vitro assay for TNF-alpha induced cell killing;

FIG. 3 shows the ability of compound B to inhibit LPS-stimulated TNF-alpha production in an in vitro model of inflammation;

FIG. 4 shows the ability of compound B to inhibit LPS-stimulated IL-6 production in an in vitro model of inflammation; and FIG. 5 shows the ability of compound B to selectively inhibit LPS-stimulated COX-2 activity in an in vitro model of inflammation.

FIG. 6 shows the effect of compound B in suppressing collagen-induced arthritis in mice.

FIG. 7 shows the effect of compound B in inhibiting LPS-induced IL-10 production.

DETAILED DESCRIPTION OF THE INVENTION

The present invention is based on the discovery that the compounds described herein appear to inhibit the production and/or activity of the pro-inflammatory cytokines TNF-alpha, interleukin-10 and IL-6 and to inhibit the activity of the enzyme COX-2.

Definitions

As utilized herein, the following terms, unless otherwise indicated, shall be understood to have the following meanings:

"Alkyl", alone or in combination, means a straight-chain or branched-chain alkyl radical containing preferably 1–20 carbon atoms, more preferably 1–10 carbon atoms, and most preferably 1–6 carbon atoms. Exemplary alkyl radicals include methyl, ethyl, n-propyl, isopropyl, n-butyl, isobutyl, sec-butyl, tert-butyl, pentyl, iso-amyl, hexyl and the like.

"Alkenyl", alone or in combination, means a straight-chain or branched-chain hydrocarbon radical having one or more double bonds, preferably 1–2 double bonds and more preferably one double bond, and containing preferably 2–20 carbon atoms, more preferably 2–10 carbon atoms, and still more preferably 2–6 carbon atoms. Exemplary alkenyl radicals include ethenyl, propenyl, 2-methylpropenyl, 1,4-butadienyl and the like.

"Alkoxy", alone or in combination, means a radical of the type "R—O—" wherein "R" is an alkyl radical as previously defined and "O" is an oxygen atom. Exemplary alkoxy radicals include methoxy, ethoxy, n-propoxy, isopropoxy, n-butoxy, iso-butoxy, sec-butoxy, tert-butoxy and the like.

"Alkoxycarbonyl", alone or in combination, means a radical of the type "R—O—C(O)—" wherein "R—O—" is an alkoxy radical as previously defined and "C(O)—" is a carbonyl radical. Exemplary alkoxycarbonyl groups include methoxycarbonyl and ethoxycarbonyl.

"Alkanoyl", alone or in combination, means a radical of the type "R—C(O)—" wherein "R" is an alkyl radical as previously defined and "—C(O)—" is a carbonyl radical. Exemplary alkanoyl radicals include acetyl, trifluoroacetyl, hydroxyacetyl, propionyl, butyryl, valeryl, 4-methylvaleryl and the like.

"Halo" or "halogen", alone or in combination, means chloro, bromo, fluoro or iodo radicals.

"Aryl", alone or in combination, means an aromatic carbocyclic radical containing about 6 to about 10 carbon atoms, which is optionally substituted with one or more substituents selected from alkyl, alkoxy, halogen, hydroxy, amino, azido, nitro, cyano, haloalkyl, carboxy, alkoxycarbonyl, cycloalkyl, alkanoylamino, amido, amidino, alkoxycarbonylamino, N-alkylamidino, alkylamino, dialkylamino, aminoalkyl, alkylaminoalkyl, dialkylaminoalkyl, N-alkylamido, N,N-dialkylamido, aralkoxycarbonylamino, alkylthio, alkylsulfinyl, alkylsulfonyl, oxo and the like. Exemplary aryl radicals include phenyl, o-tolyl, 4-methoxyphenyl, 2-(tert-butoxy)phenyl, 3-methyl-4-methoxyphenyl, 2-fluorophenyl, 2-chlorophenyl, 3-nitrophenyl, 3-aminophenyl, 3-acetamidophenyl, 2-amino-3-(aminomethyl)phenyl, 6-methyl-2-aminophenyl, 2-amino-3-methylphenyl, 4,6-dimethyl-2-aminophenyl, 4-hydroxyphenyl, 3-methyl-4-hydroxyphenyl, 4-(2-methoxyphenyl)phenyl, 2-amino-1-naphthyl, 2-naphthyl, 1-methyl-3-amino-2-naphthyl, 2,3-diamino-1-naphthyl, 4,8-dimethoxy-2-naphthyl and the like.

The reference to "optionally substituted" in the definition of the compounds of Formulas I to X is intended to include any substituent which does not negatively affect the activity of the compounds. Typical substitution includes, for example, halogen such as chlorine, nitro, amino, hydroxy, sulfonamide, cyano or the like.

Preferred Embodiments

While the invention broadly contemplates compounds of Formulas I to X as set forth earlier, a preferred group of compounds is represented by the Formula I compounds wherein two to four, preferably three, of $R_1$–$R_6$ are lower alkoxy, e.g. methoxy or ethoxy, and the remainder of $R_1$–$R_6$ are hydrogen; $R_8$ is H, lower alkyl or lower alkoxy carbonyl; Y is H, lower alkyl or lower alkoxy; Z is OH, lower alkoxy or $NH_2$, it being understood that by the references to "lower alkyl" and "lower alkoxy", carbon contents of from 1 to 8 carbons are contemplated. Particularly preferred compounds according to Formula I are those wherein $R_1$, $R_2$ and $R_4$ are methoxy; $R_3$, $R_5$, $R_6$ and $R_8$ are hydrogen, Y is hydrogen and Z is OH.

A correspondingly preferred subgroup of compounds are those according to Formula II wherein at least two, preferably three, of $R_1$ to $R_6$ are lower alkoxy, notably methoxy or ethoxy; $R_7$ is H; $R_8$ is H, lower alkyl or lower alkoxycarbonyl; Y and Y' are H, lower alkyl or lower alkoxy and Z' is O (oxo). Particularly preferred are those compounds of the Formula II structure where $R_1$, $R_2$ and $R_4$ are methoxy, $R_3$, $R_5$ and $R_6$ are hydrogen, $R_7$ is H; $R_8$ is H or ethoxycarbonyl; Y and Y' are hydrogen and Z' is O.

Generally speaking, the compounds of Formulas I to X wherein Y is hydrogen, Z is OH or Z' is O, $R_1$, $R_2$ and $R_6$ are methoxy are particularly preferred.

The following compounds are representative of the preferred subgroups for compounds within Formulas I through X according to the invention:

Formula I (Compound B)

7,8-Dimethoxy-3-(4-methoxy-phenyl)-isoquinolin-4-ol hydrochloride

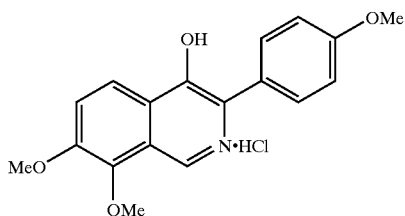

(Compound C)

7,8-Dimethoxy-3-(4-methoxy-phenyl)-isoquinoline

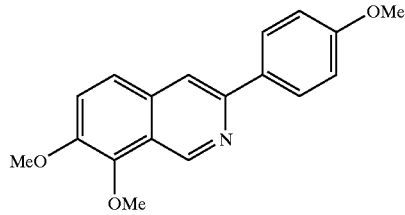

(Compound G)

5-(4-Hydroxy-7,8-dimethoxy-isoquinoline-3-yl)-2-methoxy-benzoic acid methyl ester hydrochloride

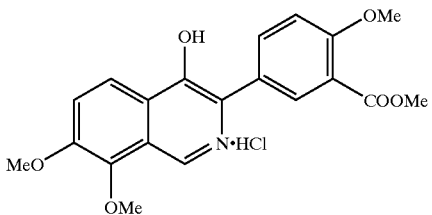

(Compound H)

7-Methoxy-3-phenyl-isoquinolin-4-ol

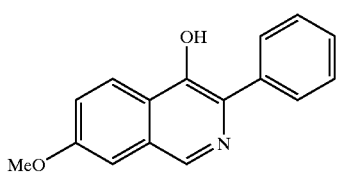

(Compound J)

8-Methoxy-3-phenyl-isoquinolin-4-ol

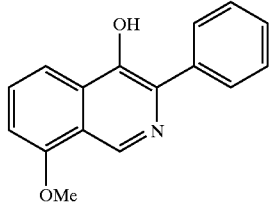

(Compound K)

5-Methoxy-1-methyl-3-phenyl-isoquinolin-4-ol

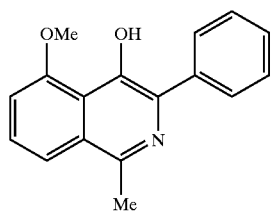

(Compound L)

3-(4-Methoxy-phenyl)-isoquinoline-4,7,8-triol

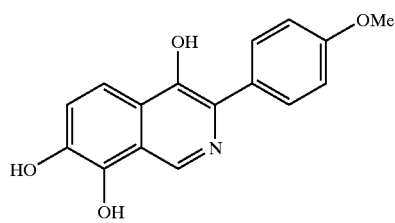

(Compound M)

7-Chloro-3-(4-hydroxy-phenyl)-isoquinolin-4-ol

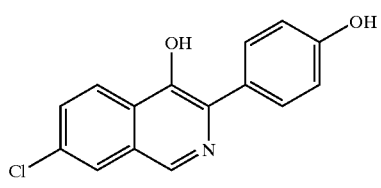

FORMULA II (Compound D)

7,8-Dimethoxy-3-(4-methoxy-phenyl)-4-oxo-3,4-dihydro-1H-isoquinoline-2-carboxylic acid ethyl ester

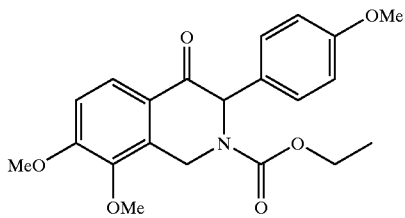

(Compound E)

7,8-Dimethoxy-3-(4-methoxy-phenyl)-2,3-dihydro-1H-isoquinoline-4-one hydrochloride

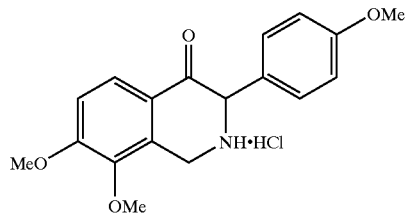

(Compound F)

5-(7,8-Dimethoxy-4-oxo-1,2,3,4-tetrahydro-isoquinolin-3-yl)-2-methoxy-benzoic acid methyl ester hydrochloride

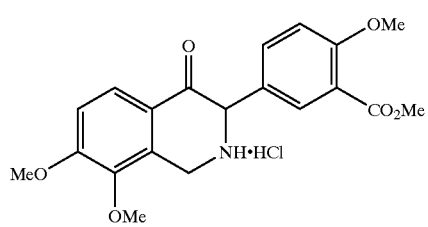

(Compound N)

7-Methoxy-3-phenyl-2,3-dihydro-1H-isoquinolin-4-one

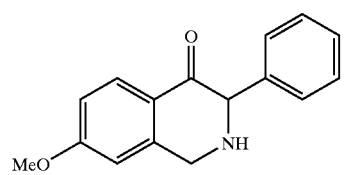

(Compound P)

8-Methoxy-3-phenyl-2,3-dihydro-1H-isoquinolin-4-one

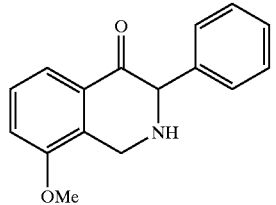

(Compound Q)

5-Methoxy-3-phenyl-2,3-dihydro-1H-isoquinolin-4-one

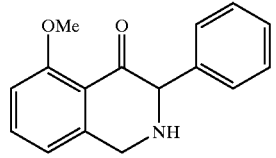

(Compound R)

6-Methoxy-3-(4-methoxy-phenyl)-2,3-dihydro-1H-isoquinolin-4-one

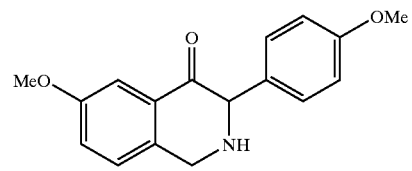

(Compound S)

1,3-Dimethyl-3-phenyl-7-trifluoromethoxy-2,3-dihydro-1H-isoquinolin-4-one

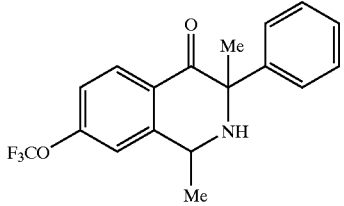

(Compound T)

7,8-Dihydroxy-3-(4-hydroxy-phenyl)-3-methyl-2,3-dihydro-1H-isoquinolin-4-one

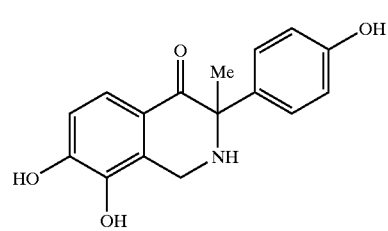

(Compound V)

7-Chloro-3-(4-hydroxy-phenyl)-2,3-dihydro-1H-isoquinolin-4-one

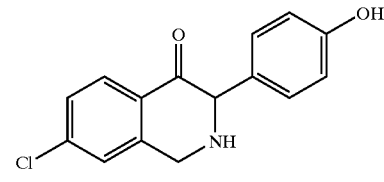

(Compound W)

8-Amino-3-(4-hydroxy-phenyl)-2,3-dihydro-1H-isoquinolin-4-one

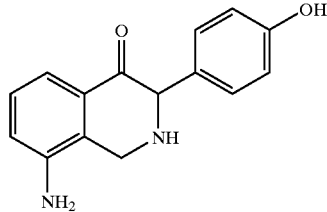

(Compound NA)

3-(4-Trifluoromethoxy-phenyl)-7-trifluoromethyl-2,3-dihydro-1H-isoquinolin-4-one

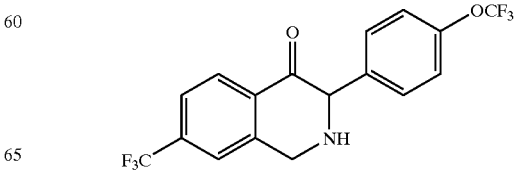

-continued (Compound NB)

7,8-Dimethoxy-3-(4-methoxy-phenyl)-3-methyl-2,3-dihydro-1H-isoquinolin-4-one

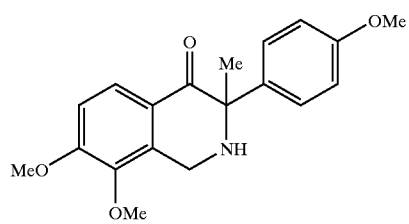

(Compound NC)

7,8-Dimethoxy-3-(4-methoxy-phenyl)-1,1,3-trimethyl-2,3-dihydro-1H-isoquinolin-4-one

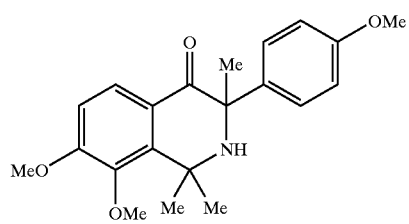

Formula III (Compound X)

6-Methoxy-3-phenyl-1,2-dihydro-isoquinolin-4-ol

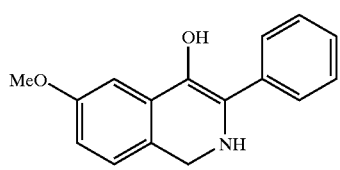

(Compound Y)

4-Methoxy-3-phenyl-1,2-dihydro-isoquinolin-7,8-diol

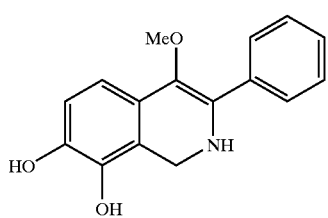

Formula IV (Compound A)

4-Hydroxy-7,8-dimethoxy-3-(4-methoxy-phenyl)-3,4-dihydro-1H-isoquinoline-2-carboxylic acid ethyl ester

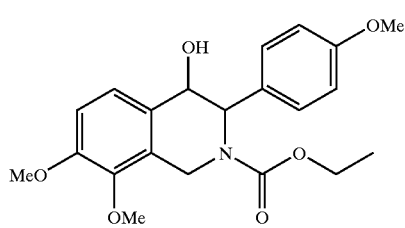

-continued (Compound Z)

1-Ethyl-3-(4-hydroxy-phenyl)-3-methyl-7-trifluoromethoxy-1,2,3,4-tetrahydro-isoquinolin-4-ol

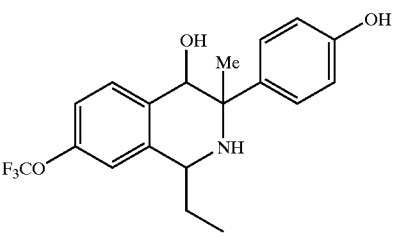

Formula V (Compound OA)

6-Methoxy-3-phenyl-isochroman-4-one

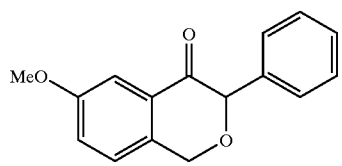

(Compound OB)

3-(4-Methoxy-phenyl)-3-methyl-7-trifluoromethoxy-isochroman-4-one

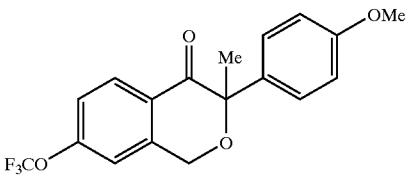

(Compound OC)

7-Methoxy-3-(4-methoxy-phenyl)-3-methyl-isochroman-4-one

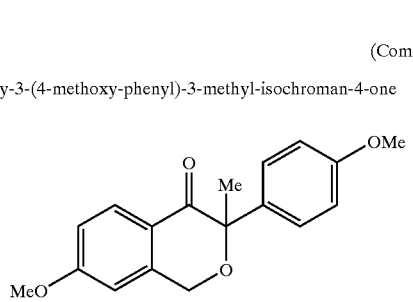

(Compound OD)

7,8-Dimethoxy-3-(4-methoxy-phenyl)-isochroman-4-one

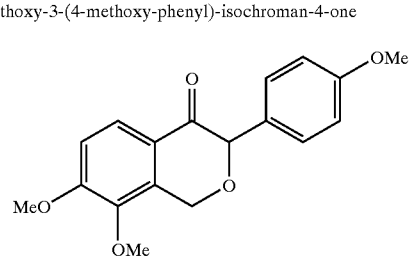

-continued (Compound OE)

6-Methyl-3-phenyl-isochroman-4-one

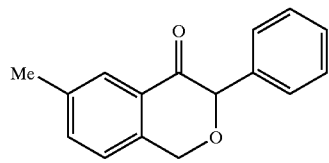

(Compound OF)

7,8-Dimethoxy-3-(4-methoxy-phenyl)-3-methyl-isochroman-4-one

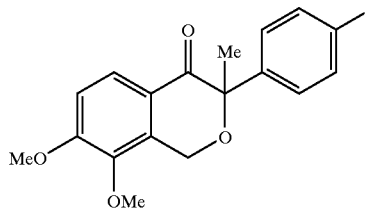

Formula VI (Compound OG)

4-(4,7,8-Trimethoxy-1-methyl-1H-isochromen-3-yl)-phenol

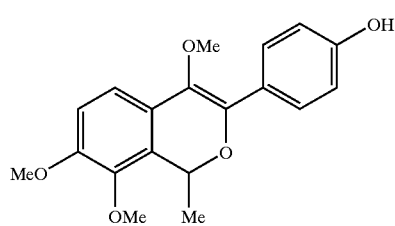

(Compound OH)

4-Methoxy-3-(4-methoxy-phenyl)-7-trifluoromethoxy-1H-isochromene

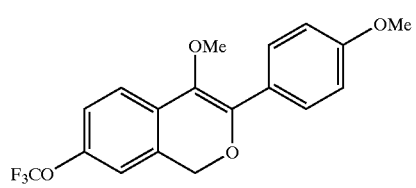

(Compound OJ)

4,7,8-Trimethoxy-3-(4-methoxy-phenyl)-1H-isochromene

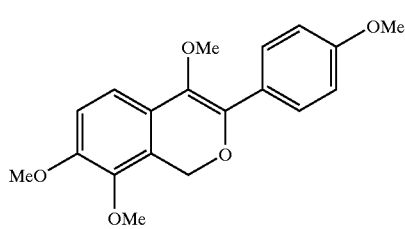

Formula VII (Compound OK)

6-Methoxy-3-phenyl-isochroman-4-ol

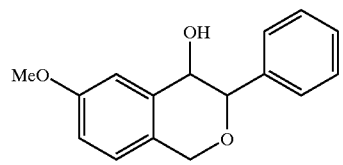

(Compound OL)

4,7-Dimethoxy-3-(4-methoxy-phenyl)-3-methyl-isochroman

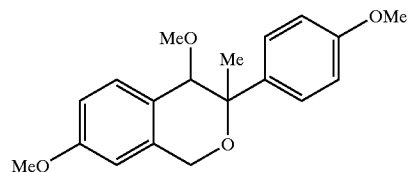

(Compound OM)

3-(4-Hydroxy-phenyl)-7,8-dimethoxy-1-methyl-isochroman-4-ol

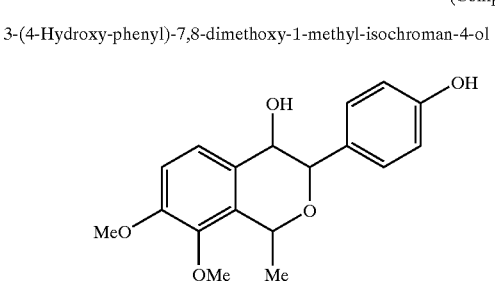

(Compound ON)

6-Methyl-3-phenyl-isochroman-4-ol

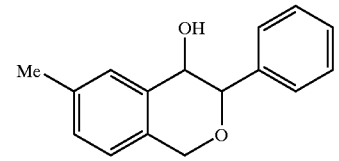

(Compound OP)

7,8-Dimethoxy-3-(4-methoxy-phenyl)-isochroman-4-ol

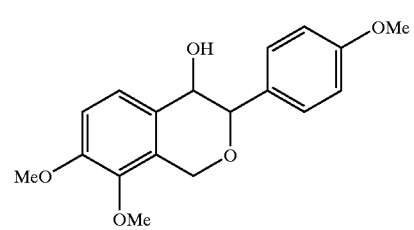

Formula VIII (Compound SA)
3-(4-Methoxy-phenyl)-3-methyl-7-trifluoromethoxy-isothiochroman-4-one (Compound SB)
6-Methoxy-3-phenyl-isothiochroman-4-one (Compound SC)
3-(4-Methoxy-phenyl)-3-methyl-7-trifluoromethoxy-isothiochroman-4-one (Compound SD)
7-Methoxy-3-(4-methoxy-phenyl)-3-methyl-isothiochroman-4-one (Compound SE)
3-(4-Hydroxy-phenyl)-7,8-dimethoxy-l-methyl-isothiochroman-4-one (Compound SF)
3,6-Dimethyl-3-phenyl-isothiochroman-4-one (Compound SG)
3-(4-Hydroxy-phenyl)-7,8-dimethoxy-isothiochroman-4-one (Compound SH)
3-(4-Hydroxy-phenyl)-7,8-dimethoxy-3-methyl-isothiochroman-4-one Formula IX (Compound SJ)
7-Fluoro-3-(4-methoxy-phenyl)-1H-isothiochromen-4-ol (Compound SK)
7,8-Dimethoxy-3-(4-methoxy-phenyl)-1H-isothiochromen-4-ol Formula X (Compound SL)
6-Methoxy-3-phenyl-isothiochroman-4-ol

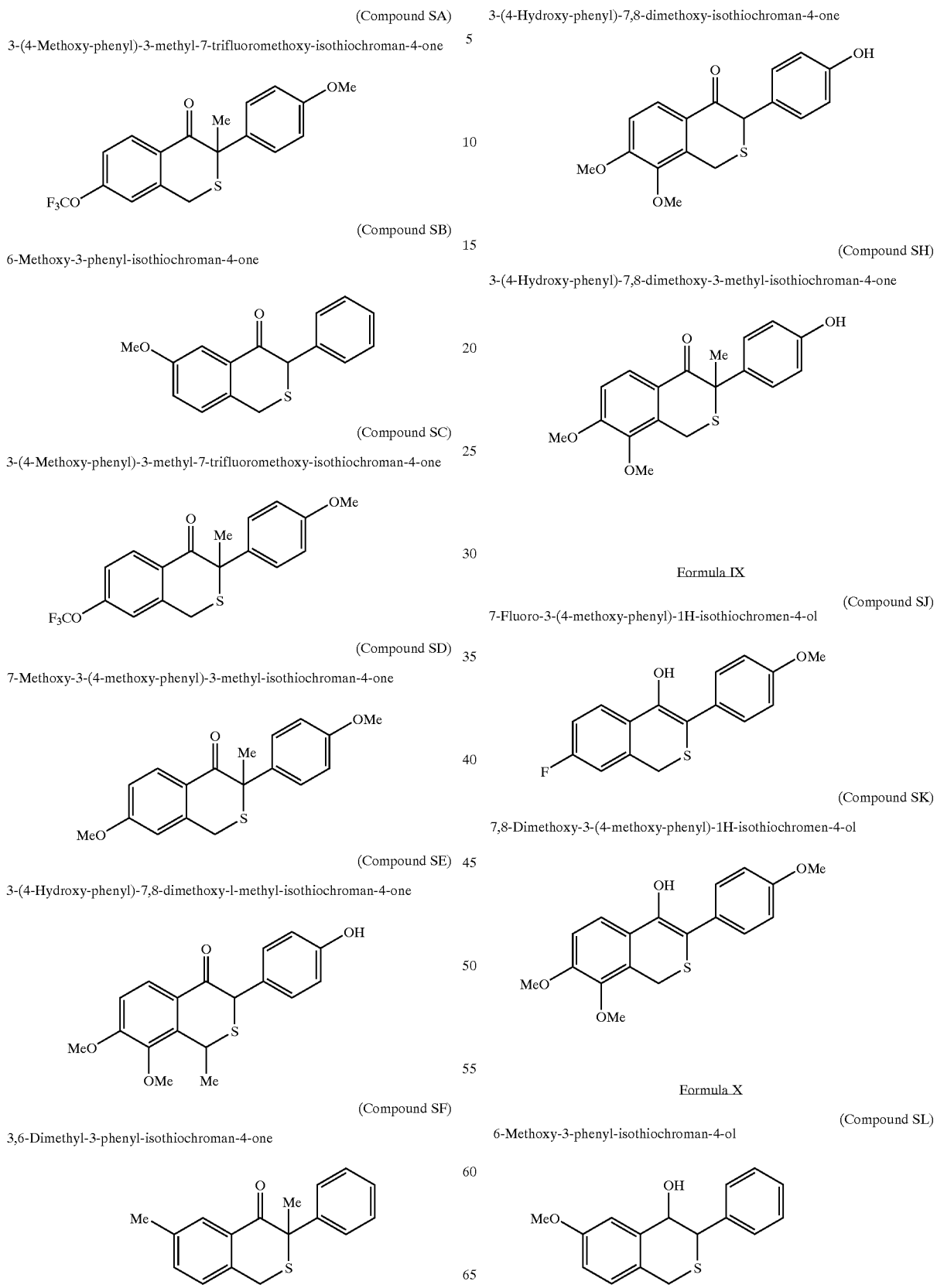

-continued (Compound SM)

4-Methoxy-3-(4-methoxy-phenyl)-7-trifluoromethoxy-isothiochroman

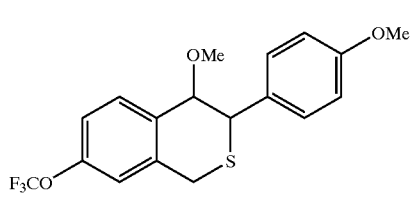

(Compound SN)

3-(4-Hydroxy-phenyl)-7,8-dimethoxy-1-methyl-isothiochroman-4-ol

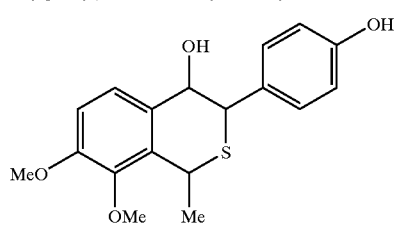

-continued (Compound SP)

3,6-Dimethyl-3-phenyl-isothiochroman-4-ol

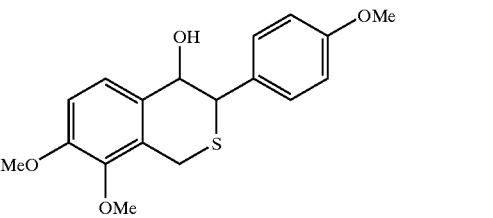

(Compound SQ)

7,8-Dimethoxy-3-(4-methoxy-phenyl)-isothiochroman-4-ol

The compounds of the invention may be obtained by synthetic methods known in the art. Preferred reaction schemes for preparing the compounds of the invention are illustrated below:

Scheme I
Synthesis of Compounds of Formulas I and III

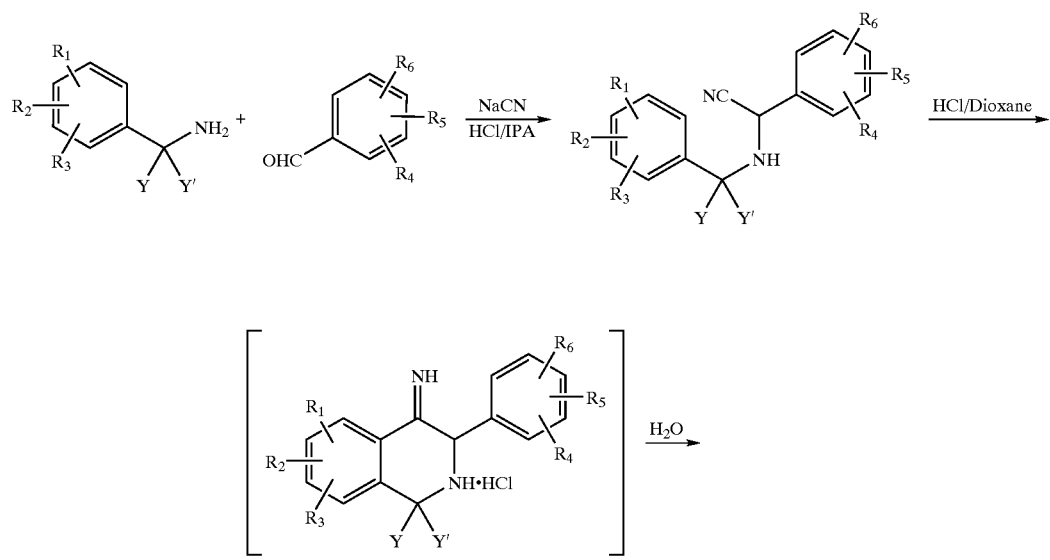

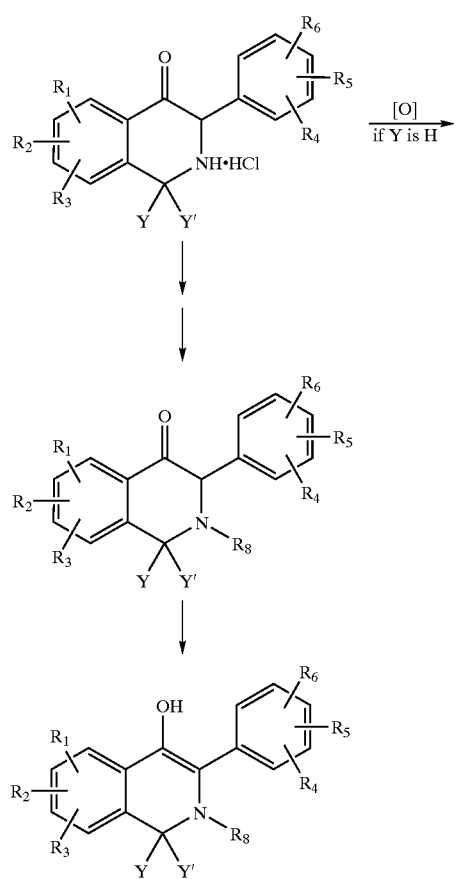
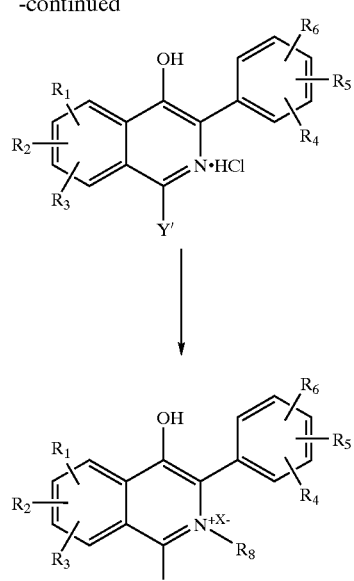
Scheme II
Synthesis of Compounds of Formulas II and IV
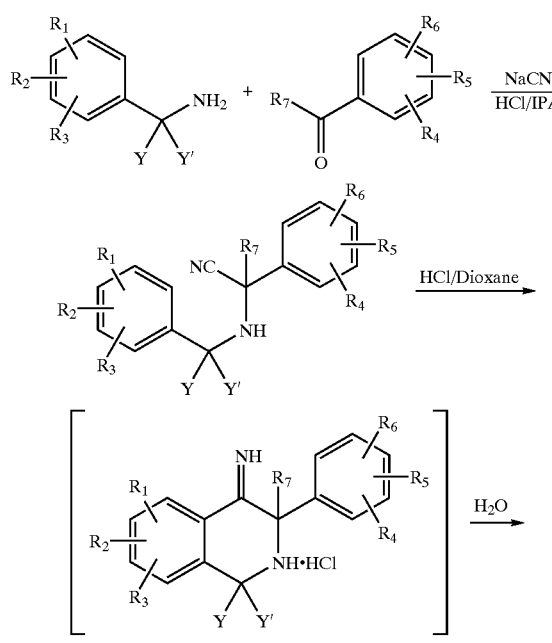
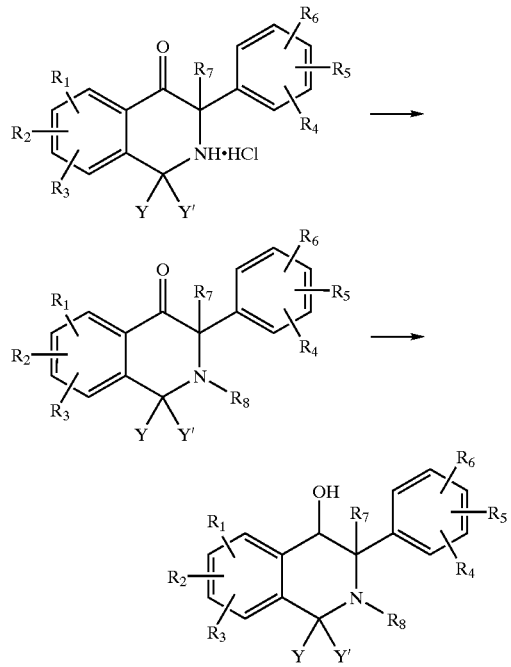
It will be appreciated that the invention is not limited to the foregoing reaction schemes as variations in the procedures will be evident to those in the art.

Some of the compounds of the invention contain one or more chiral centers and each center may exist in different configurations. Thus, the compounds of Formulas I to X can form stereoisomers. The invention encompasses both the individual isomers and mixtures, including racemates, thereof. In addition, both the preparation of individual isomers by stereospecific synthesis techniques and the preparation of mixtures of isomers, which may then be resolved by conventional methods or used as is, are contemplated by the invention.

Many of the compounds of the present invention are capable of forming pharmaceutically acceptable salts, such as acid and base addition salts, as well as solvates, such as hydrates and alcoholates. All such pharmaceutically acceptable salts and solvates are contemplated by the present invention and incorporated herein. Representative pharmaceutically acceptable acid addition salts of the free base compounds of Formulas I and II include chloride, bromide, iodide, sulfate, pyrosulfate, bisulfate, sulfite, bisulfite, nitrate, phosphate, monohydrogenphosphate, dihydrogenphosphate, metaphosphate, pyrophosphate, acetate, trifluoroacetate, propionate, isobutyrate, oxalate, malonate, succinate, fumarate, maleate, benzoate, chlorobenzoate, methylbenzoate, dinitrobenzoate, phthalate, benzenesulfonate, toluenesulfonate, phenylacetate, citrate, lactate, maleate, tartrate, methanesulfonate, and the like. Also contemplated by the present invention are salts of amino acids such as arginate and the like and gluconate, galacturonate and the like. The acid addition salts may be formed by conventional methods using inorganic acids, such as hydrochloric acid, sulfuric acid, nitric acid, phosphoric acid, and the like, or organic acids, such as aromatic acids, aliphatic sulfonic acids, aromatic sulfonic acids, aliphatic monocarboxylic acids, aliphatic dicarboxylic acids, phenyl-substituted alkanoic acids, hydroxy alkanoic acids, and the like.

Pharmaceutically acceptable base addition salts may be formed by conventional methods using metals, such as sodium, potassium, magnesium, calcium, and the like, or using amines, such as diethanolamine, dicyclohexylamine, ethylenediamine, dibenzylethylenediamine, chloroprocaine, choline, and the like.

Compounds within the scope of the present invention are inhibitors of the production and/or activity of the pro-inflammatory cytokines tumor necrosis factor-alpha (TNF-alpha) and interleukin-6 (IL-6), interleukin-10 (IL-10), as well as selective inhibitors of the activity of the enzyme cyclooxygenase-2 (COX-2). The compounds disclosed herein exhibit useful pharmacological activity and accordingly may be incorporated into pharmaceutical compositions and used in the treatment and/or prevention of inflammation, inflammatory diseases, immunologic disorders, infectious diseases, malignant diseases and other conditions mediated by TNF-alpha, IL-6, interleukin-10 (IL-10) and/or COX-2. By way of example, without limitation, compounds within the scope of the present invention may be used in the treatment of the following conditions: rheumatoid arthritis, cachexia, septic shock syndrome, osteoarthritis, inflammatory bowel disease, Crohn's disease, ulcerative colitis, Behcet's disease, Kawasaki disease, cerebral malaria, adult respiratory distress syndrome, asbestosis, silicosis, pulmonary sarcoidosis, asthma, AIDS, meningitis, psoriasis, contact dermatitis, allergy, graft versus host reaction, multiple sclerosis, systemic lupus erythematosus, diabetes, myasthenia gravis, leprosy, hypertoxic alveolar injury, reperfusion injury, atherosclerosis, coronary heart disease, steroid withdrawal syndrome, vasopressin secretion disorders, osteoporosis, hyperparathyroidism, sex-steroid deficiency, familial adenomatous polyposis and colorectal cancer.

The compounds of the invention may be administered to animals, preferably mammals, and most preferably humans, using any convenient administration technique, including intravenously, intradermally, intramuscularly, subcutaneously, orally, rectally, transdermally, topically, by inhalation, and the like. The dosage delivered may be determined by a physician or qualified medical professional and will depend on the route of administration, the desired therapeutic effect, the duration of treatment, and the condition of the patient, but will generally range from 1 to 500 mg/70 kg human body weight/day.

The compounds of the invention may be used in formulations using acceptable pharmaceutical vehicles for enteral, or parenteral administration, such as, for example, water, alcohol, gelatin, gum arable, lactose, amylase, magnesium stearate, talc, vegetable oils, polyalkylene glycol, and the like. The compounds can be formulated in solid form, for example, as tablets, capsules, dragees and suppositories, or in liquid form, for example, as solutions, suspensions and emulsions.

The following examples are presented by way of illustration, and are not intended to limit the invention in any way.

EXAMPLE 1

Synthesis of Representative Compounds

Compounds B and E, representative of the compounds of Formula I and II, respectively, were synthesized using the method illustrated below as Scheme III.

2,3-Dimethoxybenzylamine (6.06 mL, 41.0 mmol) was dissolved in anhydrous isopropanol (50 mL) at room temperature and concentrated HCl (3.3 mL, 1.0 equiv) was added all at once with good stirring. 4-Methoxybenzaldehyde (5.0 mL, 1.0 equiv) was then added, followed by sodium cyanide (2.4 g, 1.2 equiv). The flask was stoppered and stirred at room temperature overnight. The solvent was roto-evaporated (caution: HCN vapors) and the residue triturated with 300 mL EtOAc, dried ($Na_2SO_4$) and filtered (caution: solid contains excess NaCN). The filtrate was evaporated. The residue was dissolved in 65 ml $CH_2Cl_2$, and HCl (65 mL, 4 N in dioxane) was added. The flask was stoppered and stirred at room temperature for 2 days. $CH_2Cl_2$ was roto-evaporated. To the remainder was added 65 mL $H_2O$ with stirring for 2 h. The precipitate was collected on a Buchner funnel and rinsed with isopropanol, then EtOAc and air-dried. The product was a pale yellow solid, 7.5 g of 52% pure compound E.

To a two-liter Erlenmeyer flask, open to the atmosphere, Compound E (25 g) was added, followed by absolute ethanol (500 mL) and deionized water (500 mL), and the mixture was stirred for 48 hr at room temperature. The solvent was slowly evaporated under reduced pressure to near dryness. The residue was dissolved by boiling in a minimal amount of absolute ethanol (300 to 400 mL), and the solution was then incubated for 48 hr at 0° C. to allow recrystallization. The crystals of the resulting Compound B were filtered, rinsed with hexane until the filtrate became colorless (~500 mL) and then dried overnight in an oven at 50° C. The dried, purified Compound B (15.7 g, yellow solid, HPLC purity ~99%) was obtained in 62.8% yield for the final step (see Scheme III).

Analysis: $^1$H-NMR, 400 MHz (DMSO-$d_6$): δ9.02 (s, 1H), 8.43 (d, J=9.2 Hz, 1H), 8.10 (d, J=8.8 Hz, 1H), 7.81 (d, J=6.8 Hz, 2H), 7.15 (d, J=7.2 Hz, 2H), 4.06 (s, 6H), 3.86 (s, 3H).

SCHEME III

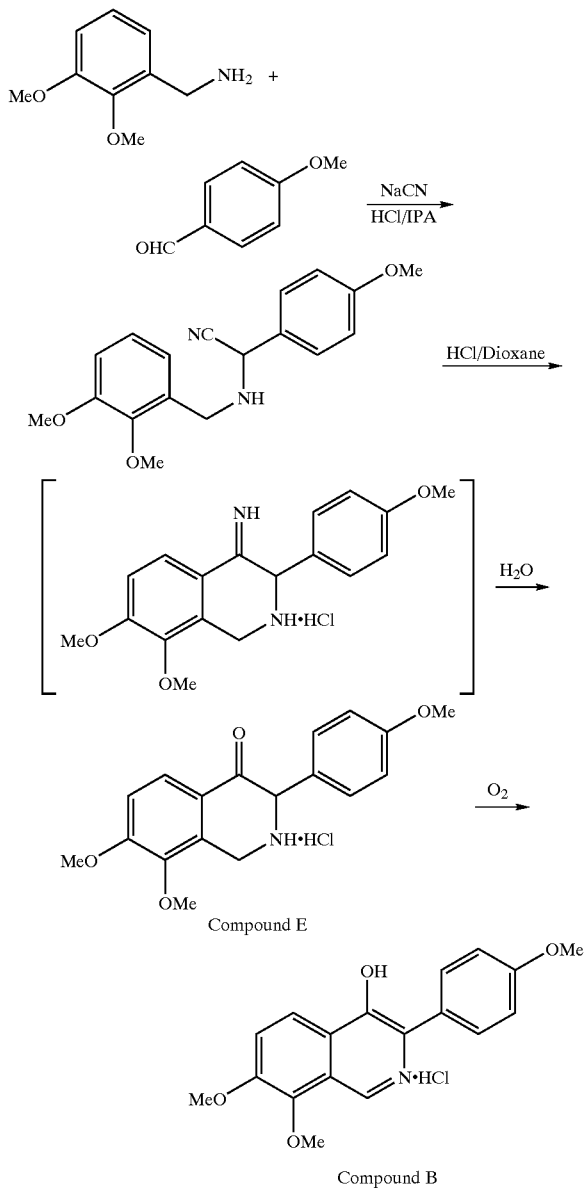

EXAMPLE 2

Inhibition of TNF-alpha Induced Cell Killing

Compounds B and E were tested for their ability to inhibit TNF-alpha induced killing of cultured mouse fibrosarcoma cells. WEHI-13VAR cells were grown in buffered RPMI-1640 medium containing 3% FBS and assayed for TNF-alpha induced cell death as described by Khabar et al. (Immunol Lett 46:107–10, 1995). Cells were co-incubated for 20 hr with 100 pg/ml (FIG. 1A) or 1 pg/ml (FIG. 1B) of TNF-alpha and 100 µg/ml of berberine, compound B or compound E. Controls included cells receiving TNF-alpha but no drug, as well as cells receiving no TNF-alpha and treated with or without NP-40 lysis buffer. Cell viability was assayed using the dye MTT (3-(4,5-dimethylthiozol-2-yl)- 2,5-diphenyl tetrazolium bromide) as described. As shown in FIG. 1, co-incubation with compound E or B inhibited TNF-alpha induced cell killing (i.e., increased cell viability) relative to untreated or berberine-treated cells.

EXAMPLE 3

Dose Response of Inhibition of TNF-alpha Induced Cell Killing

The dose response was measured for the ability of compound B to inhibit TNF-alpha induced killing of cultured mouse fibrosarcoma cells. In this experiment, the inhibitory action of compound B was compared to that of a chimeric recombinant protein dimer containing soluble TNF receptor fused to the Fc portion of immunoglobulin heavy chain (Mohler KM et al., J Immunol 151:1548–61,1993), a known antagonist of TNF-alpha mediated cell killing. WEHI-13VAR cells were grown in buffered RPMI-1640 medium containing 3% FBS and assayed for TNF-alpha induced cell death as described by Khabar et al. (Immunol Lett 46:107–10, 1995). Cells were co-incubated for 20 hr with 100 pg/ml, 50 pg/ml or no TNF-alpha and varying concentrations of soluble TNF receptor/Fc chimera (FIG. 2A) or compound B (FIG. 2B). Cell viability was assayed using the dye MTT (3-(4,5-dimethylthiozol-2-yl)-2,5-diphenyl tetrazolium bromide) as described. As shown in FIG. 2B, for both concentrations of TNF-alpha tested, the inhibition of TNF-alpha induced cell killing (i.e., increased cell viability) was proportional to the dose of compound B up to a concentration of 10 µM, at which concentration the maximal inhibitory effect was attained.

EXAMPLE 4

Inhibition of LPS-induced TNF-alpha Production

The ability of compound B to inhibit TNF-alpha production was examined in a standard in vitro model of inflammation—the murine macrophage-like cell line RAW264.7 stimulated with lipopolysaccharides (LPS). RAW264.7 cells were grown in RPMI-1640 medium containing 3% FBS and pre-incubated for 1 hr at 37° C. with varying concentrations (1, 3, 10, 30 or 100 µM) of compound B. LPS (0.1 µg/ml) was then added, and the cells were further incubated for 6 hr at 37° C. in a 5% carbon dioxide atmosphere. Cell supernatants were then collected, aliquoted, and assayed for TNF-alpha by ELISA with anti-TNF-alpha antibody. As shown in FIG. 3, treatment with compound B inhibited LPS-induced TNF-alpha production by nearly 50%.

EXAMPLE 5

Inhibition of LPS-induced IL-6 Production

The ability of compound B to inhibit IL-6 production was also examined in LPS-stimulated RAW cells. RAW264.7 cells were grown in RPMI-1640 medium containing 3% FBS and pre-incubated for 1 hr at 37° C. with varying concentrations (1, 3, 10, 30 or 100 µM) of compound B. LPS (0.1 µg/ml) was then added, and the cells were further incubated for 6 hr at 37° C. in a 5% carbon dioxide atmosphere. Cell supernatants were then collected, aliquoted, and assayed for IL-6 by ELISA with anti-IL-6 antibody. As shown in FIG. 3, treatment with compound B inhibited LPS-induced IL-6 production by up to 60%.

EXAMPLE 6

Selective Inhibition of LPS-induced COX-2 Activity

The ability of compound B to selectively inhibit COX-2 activity was also examined in LPS-stimulated RAW cells. In this experiment, the inhibitory effect of compound B was compared to that of dexamethasone, a potent inhibitor of COX-2 expression. RAW264.7 cells were grown in RPMI-1640 medium containing 3% FBS and pre-incubated for 1 hr at 37° C. with compound B (1, 3, 10, 30 or 100 $\mu$M), dexamethasone (Dex, 1 $\mu$M), or without drug. After 1 hr LPS (0.1 $\mu$g/ml) was added, and the cells were further incubated for 6 hr at 37° C. Control cells received neither drug nor LPS. Cells were collected, lysed and assayed for cyclooxygenase activities essentially according to the method of Brideau et al. (Inflamm Res 45:68–74, 1996). COX-2 activity was measured using the Biotrak Prostaglandin E2 (PGE2) EIA Kit, and COX-1 activity was determined using the Biotrak Thromboxane B2 (TXB2) EIA Kit, both from Amersham Pharmacia Biotech (Piscataway, N.J.). As with treatment with dexamethasone, pre-incubation with the higher concentrations of compound B completely and selectively abrogated the inducible COX-2 activity (FIG. 5A) while having no effect on the constitutively expressed COX-1 activity (FIG. 5B).

EXAMPLE 7

Suppression of Collagen-induced Arthritis in Mice

The ability of compound B to reduce inflammation in an animal model of arthritis was also studied. Arthritis was induced by intradermal administration of collagen (100 $\mu$g/mice) in complete adjuvant in male DBA/1 Lac mice 7 weeks old. The booster immunization (100 $\mu$g/mice) in incomplete adjuvant was given subcutaneously on day 21. Two days later, when arthritic scores were around 1, animals were divided into two groups. One group received 50 mg/kg dose of compound B orally for 17 days daily. The second group received 10% PEG in water and was used as a vehicle-treated group. Body weight (FIG. 6, panel A), clinical score (FIG. 6, panel B), the number of joints affected (FIG. 6, panel C) and paw thickness (FIG. 6, panel D) were monitored 24 hours after drug administration during the treatment period. As shown in FIG. 6, mice treated with compound B showed significantly lower clinical scores, fewer joints affected, and reduced paw thickness when compared to the vehicle-treated group. No change in body weight was observed between the vehicle and the treatment groups.

EXAMPLE 8

Inhibition of LPS-induced IL-10 Production in Human PBC

Human peripheral blood mononuclear cells (PBMC) were purified from human blood using Ficoll-Paque PLUS separation medium (Amersham Pharmacia Biotech) according to the manufacturer's recommended protocol. After centrifugation, the central PBMC layer was collected, washed twice with phosphate buffered saline (PBS) and then plated in a 96-well plate at a density of 2×10$^5$ cells/well in RPMI-1640 medium containing 10% FBS. The cells were preincubated with dexamethasone (1 $\mu$M) or Compound B (1, 10, 30 or 100 $\mu$M) for 1 hr and then challenged with LPS (1 $\mu$g/ml) for 20 hr. Cells receiving no drug treatment, incubated with or without LPS, served as controls. The cell supernatants were collected, and the amount of IL-10 in each was measured by standard ELISA. As shown in FIG. 7, preincubation of cells with Compound B resulted in a dose-dependent inhibition of LPS-induced IL-10 production. To confirm that the observed decrease in IL-10 was not due to cytotoxicity, the PBMC were plated in a separate plate, incubated for 20 hr with the same range of doses of Compound B, and the cell viability was assessed by a standard MTS dye exclusion assay (4-hr incubation with MTS). There was no significant loss in cell viability over the range of doses tested (data not shown).

It will be appreciated from the foregoing that various modifications of the invention are contemplated beyond the specific exemplification given herein. Accordingly, the invention is defined by the following claims where:

We claim:

1. A compound having a structure selected from Formulas I to IV:

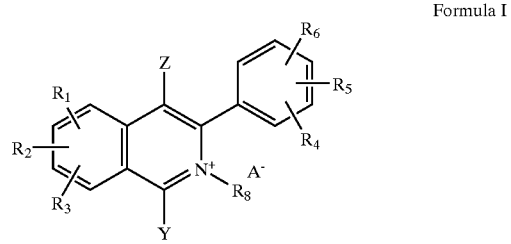

Formula I

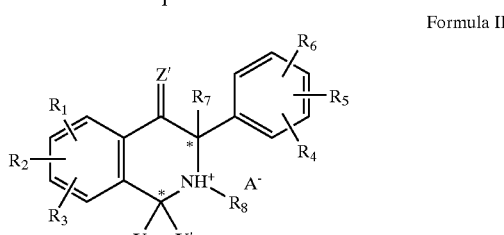

Formula II

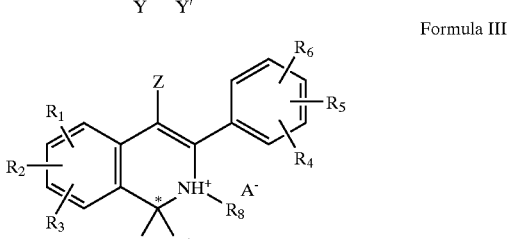

Formula III

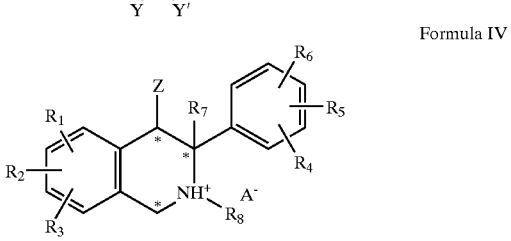

Formula IV wherein the stereocenters marked with an asterisk (*) may be R— or S— and $R_1$, $R_2$, $R_3$, $R_4$, $R_5$, and $R_6$ are independently H; optionally substituted $C_1$–$C_{20}$ linear or branched alkyl; optionally substituted $C_2$–$C_{20}$ linear or branched alkenyl; optionally substituted $C_6$–$C_{20}$ aryl, linear or branched alkylaryl, linear or branched alkenylaryl; COOR where R is H, optionally substituted $C_1$–$C_{20}$ alkyl, optionally substituted $C_2$–$C_{20}$ alkenyl or optionally substituted $C_6$–$C_{10}$ aryl, or a pharmaceutically acceptable counter-ion; CONR'R", where R' and R" are independently H, optionally substituted $C_1$–$C_{20}$ alkyl, optionally substituted $C_2$–$C_{20}$ alkenyl or optionally substituted $C_6$–$C_{10}$ aryl or where NR'R" represents a cyclic moiety; $NH_2$; optionally substituted $C_1$–$C_{20}$ alkylamino, bis (alkylamino), cycloalkylamino or cyclic amino; OH;

optionally substituted $C_1$–$C_{20}$ alkoxy; optionally substituted $C_1$–$C_{20}$ alkanoyl; optionally substituted $C_1$–$C_{20}$ acyloxy; halo; optionally substituted $C_1$–$C_{20}$ alkylcarboxylamino; cyano; nitro; $SO_2NR'''R''''$ where R''' and R'''' are independenyly H, $C_1$–$C_{20}$ alkyl or aryl; $SO_2R'''$ where R''' is H, $C_1$–$C_{20}$ alkyl or aryl; $SO_3R'''$ where R''' is H, $C_1$–$C_{20}$ alkyl or aryl; or $C_4$–$C_8$ heterocycles; or two of $R_1$, $R_2$, $R_3$, $R_4$, $R_5$, or $R_6$ together represent a ring;

$R_7$ is
H in which case the compounds may be in tautomeric form or optionally substituted $C_1$–$C_{20}$ linear or branched alkyl;

$R_8$ is
H; OH or O in the case of Formula I compounds; optionally substituted $C_1$–$C_{20}$ linear or branched alkyl; optionally substituted $C_2$–$C_{20}$ linear or branched alkenyl; optionally substituted $C_6$–$C_{20}$ aryl, linear or branched alkylaryl, linear or branched alkenylaryl; COOR where R is H, optionally substituted $C_1$–$C_{20}$ alkyl, optionally substituted $C_2$–$C_{20}$ alkenyl or optionally substituted $C_6$–$C_{10}$ aryl, or a pharmaceutically acceptable counter-ion; CONR'R", where R' and R" are independently H, optionally substituted $C_1$–$C_{20}$ alkyl, optionally substituted $C_2$–$C_{20}$ alkenyl or optionally substituted $C_6$–$C_{10}$ aryl or where NR'R" represents a cyclic moiety; or optionally substituted alkanoyl, alkenoyl, aroyl, alkylaroyl or alkenylaroyl; and "$A^-$" represents a pharmaceutically acceptable counter-ion; or
$R_8$ is absent, in which case the nitrogen does not bear a positive charge and the counter-ion "$A^-$" is not present;

Y and Y' are independently
H; optionally substituted $C_1$–$C_{20}$ linear or branched alkyl; optionally substituted $C_2$–$C_{20}$ linear or branched alkenyl; optionally substituted $C_6$–$C_{20}$ aryl, linear or branched alkylaryl, linear or branched alkenylaryl; COOR where R is H, optionally substituted $C_1$–$C_{20}$ alkyl, optionally substituted $C_2$–$C_{20}$ alkenyl or optionally substituted $C_6$–$C_{10}$ aryl or a pharmaceutically acceptable counter-ion; CONR'R", where R' and R" are independently H, optionally substituted $C_1$–$C_{20}$ alkyl, optionally substituted $C_2$–$C_{20}$ alkenyl or optionally substituted $C_6$–$C_{10}$ aryl or where NR'R" represents a cyclic moiety; $NH_2$; optionally substituted $C_1$–$C_{20}$ alkylamino, bis (alkylamino), cycloalkylamino or cyclic amino; OH; optionally substituted $C_1$–$C_{20}$ alkoxy; optionally substituted $C_1$–$C_{20}$ alkanoyl; optionally substituted $C_1$–$C_{20}$ acyloxy; halo; optionally substituted $C_1$–$C_{20}$ alkylcarboxylamino; cyano; nitro; $SO_2NR'''R''''$ where R''' and R'''' are independently H, $C_1$–$C_{20}$ alkyl or aryl; $SO_2R'''$ where R''' is H, $C_1$–$C_{20}$ alkyl or aryl; $SO_3R'''$ where R''' is H, $C_1$–$C_{20}$ alkyl or aryl; or $C_4$–$C_8$ heterocycles; or Y and Y' together may be joined in a ring;

Z is
OH; optionally substituted $C_1$–$C_{20}$ alkoxy; NR'R", where R' and R" are independently H, optionally substituted $C_1$–$C_{20}$ alkyl, optionally substituted $C_2$–$C_{20}$ alkenyl or optionally substituted $C_6$–$C_{10}$ aryl or where NR'R" represents a cyclic moiety; or SR'''' where R'''' is H, optionally substituted $C_1$–$C_{20}$ alkyl, optionally substituted $C_2$–$C_{20}$ alkenyl or optionally substituted $C_6$–$C_{10}$ aryl;

Z' is
O; S; or NR'''', where R'''' is H, optionally substituted $C_1$–$C_{20}$ alkyl, optionally substituted $C_2$–$C_{20}$ alkenyl or optionally substituted $C_6$–$C_{10}$ aryl;

with the provisos that in Formula I,
when Y is H, then Z is OH, $R_8$ is H, and $R_1$, $R_2$ and $R_3$ are not 6-methoxy; when Y is methyl or substituted benzyl, then $R_1$, $R_2$ and $R_3$ do not comprise 6,7-dimethoxy or 5,6,7-trimethoxy or 6,7,8-trimethoxy; and when Z is OH, at least one $R_1$, $R_2$, $R_3$, $R_4$, $R_5$ and $R_6$ is not H;

in Formula II,
when Y is H and Y' is H, then Z' is O, $R_8$ is H, and $R_1R_2$ and $R_3$ are not 6-methoxy;
when Y is H and Y' is methyl or substituted benzyl, then $R_1$, $R_2$ and $R_3$ do not comprise 6,7-dimethoxy or 5,6,7-trimethoxy or 6,7,8-trimethoxy; and
when Z' is O, at least one of $R_1$, $R_2$, $R_3$, $R_4$, $R_5$, $R_6$ and $R_7$ is not H;

in Formula III,
when Y is H and Y' is H, then Z is OH, $R_8$ is H, and $R_1$, $R_2$ and $R_3$ are not 6-methoxy;
when Y is H and Y' is methyl or substituted benzyl, then $R_1$, $R_2$ and $R_3$ do not comprise 6,7-dimethoxy or 5,6,7-trimethoxy or 6,7,8-trimethoxy; and
when Z is OH or alkoxy, at least one of $R_1$, $R_2$, $R_3$, $R_4$, $R_5$ and $R_6$ is not H;

in Formula IV,
when Y is H and Y' is H, then Z is OH, $R_8$ is H, and $R_1$, $R_2$ and $R_3$ are not 6-methoxy;
when Y is H and Y' is methyl or substituted benzyl, then $R_1$, and $R_2$ and $R_3$ do not comprise 6,7-dimethoxy or 5,6,7-trimethoxy or 6,7,8-trimethoxy; and
when Z is OH, at least one of $R_1$, $R_2$, $R_3$, $R_4$, $R_5$, $R_6$ and $R_7$ is not H.

2. A compound according to claim 1 which is of Formula I.

3. A compound according to claim 1 which is of Formula II.

4. A compound according to claim 1 which is of Formula III.

5. A compound according to claim 1 which is of Formula IV.

6. A compound according claim 1 of Formula I wherein two to four of $R_1$–$R_6$ are lower alkoxy, and the remainder of $R_1$–$R_6$ are hydrogen; $R_8$ is H, lower alkyl or lower alkoxy carbonyl; Y is H, lower alkyl or lower alkoxy; Z is OH, lower alkoxy or $NH_2$.

7. A compound according to claim 6 wherein $R_1$, $R_2$ and $R_4$ are methoxy; $R_3$, $R_5$, $R_6$ and $R_8$ are hydrogen; Y is hydrogen and Z is OH.

8. A compound according to claim 1 of Formula II wherein at least two of $R_1$ to $R_6$ are lower alkoxy; $R_7$ is H; $R_8$ is H, lower alkyl or lower alkoxycarbonyl; Y and Y' are H, lower alkyl or lower alkoxy and Z' is O.

9. A compound according to claim 8 wherein $R_1$, $R_2$ and $R_4$ are methoxy; $R_3$, $R_5$ and $R_6$ are hydrogen; $R_7$ is H; $R_8$ is H or ethoxycarbonyl, Y and Y' are hydrogen and Z' is O.

10. A compound according to claim 1 selected from the group consisting of:
7,8-Dimethoxy-3-(4-methoxy-phenyl)-isoquinolin-4-ol hydrochloride
7,8-Dimethoxy-3-(4-methoxy-phenyl)-isoquinoline
5-(4-Hydroxy-7,8-dimethoxy-isoquinoline-3-yl)-2-methoxy-benzoic acid methyl ester hydrochloride
7-Methoxy-3-phenyl-isoquinolin-4-ol
8-Methoxy-3-phenyl-isoquinolin-4-ol 5-Methoxy-1-methyl-3-phenyl-isoquinolin-4-ol 3-(4-Methoxy-phenyl)-isoquinoline-4,7,8-triol 7-Chloro-3-(4-hydroxy-phenyl)-isoquinolin-4-ol 7,8-Dimethoxy-3-(4-methoxy-phenyl)-4-oxo-3,4-dihydro-1H-isoquinoline-2-carboxylic acid ethyl ester 7,8-Dimethoxy-3-(4-methoxy-phenyl)-2,3-dihydro-1H-isoquinoline-4-one hydrochloride 5-(7,8-Dimethoxy-4-oxo-1,2,3,4-tetrahydro-isoquinolin-3-yl)-2-methoxy-benzoic acid methyl ester hydrochloride 7-Methoxy-3-phenyl-2,3-dihydro-1H-isoquinolin-4-one 8-Methoxy-3-phenyl-2,3-dihydro-1H-isoquinolin-4-one 5-Methoxy-3-phenyl-2,3-dihydro-1H-isoquinolin-4-one 6-Methoxy-3-(4-methoxy-phenyl)-2,3-dihydro-1H-isoquinolin-4-one 1,3-Dimethyl-3-phenyl-7-trifluoromethoxy-2,3-dihydro-1H-isoquinolin-4-one 7,8-Dihydroxy-3-(4-hydroxy-phenyl)-3-methyl-2,3-dihydro-1H-isoquinolin-4-one 7-Chloro-3-(4-hydroxy-phenyl)-2,3-dihydro-1H-isoquinolin-4-one 8-Amino-3-(4-hydroxy-phenyl)-2,3-dihydro-1H-isoquinolin-4-one 6-Methoxy-3-phenyl-1,2-dihydro-isoquinolin-4-ol 4-Methoxy-3-phenyl-1,2-dihydro-isoquinolin-7,8-diol 4-Hydroxy-7,8-dimethoxy-3-(4-methoxy-phenyl)-3,4-dihydro-1$_H$-isoquinoline-2-carboxylic acid ethyl ester 1-Ethyl-3-(4-hydroxy-phenyl)-3-methyl-7-trifluoromethoxy-1,2,3,4-tetrahydro-isoquinolin-4-ol 3-(4-Trifluoromethoxy-phenyl)-7-trifluoromethyl-2,3-dihydro-1H-isoquinolin-4-one 7,8-Dimethoxy-3-(4-methoxy-phenyl)-3-methyl-2,3-dihydro-1H-isoquinolin-4-one 7,8-Dimethoxy-3-(4-methoxy-phenyl)1,1,3-trimethyl-2,3-dihydro-1H-isoquinolin-4-one.

11. A compound according to claim 1 which in hydrochloride salt form is represented by the formula:

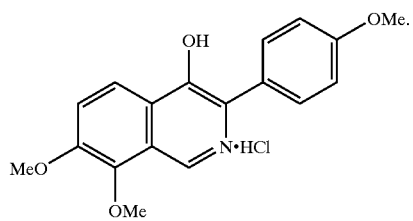

12. A compound according to claim 1 which in hydrochloride salt form is represented by the formula:

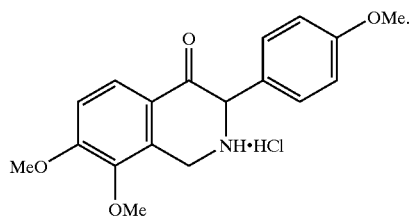

13. A compound according to claim 1 as represented by the formula:

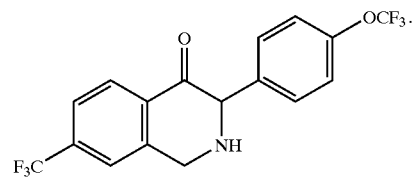

14. A compound according to claim 1 as represented by the formula:

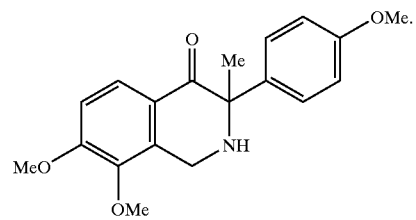

15. A compound according to claim 1 as represented by the formula:

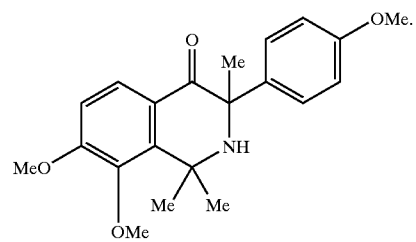

16. A method of inhibiting the activity of at least one of TNF-alpha, IL-6, IL-10 and COX-2 which comprises administering to a mammal in need of such inhibition, an effective amount of a compound according to claim 1.

17. A method of treating inflammation, inflammatory diseases and other diseases mediated by at least one of TNF-alpha, IL-6, IL-10 and COX-2 which comprises administering to a mammal in need of such treatment, an effective amount of a compound according to claim 1.

18. A pharmaceutical composition in unit dosage form comprising a compound according to claim 1 together with a pharmaceutically acceptable carrier thereof.

19. A method of inhibiting the activity of at least one of TNF-alpha, IL-6, IL-10 and COX-2 which comprises administering to a mammal in need of such inhibition, an effective amount of a compound according to claim 10.

20. A method of treating inflammation, inflammatory diseases and other diseases mediated by at least one of TNF-alpha, IL-6, IL-10 and COX-2 which comprises administering to a mammal in need of such treatment, an effective amount of a compound according to claim 10.

21. A pharmaceutical composition in unit dosage form comprising a compound according to claim 10 together with a pharmaceutically acceptable carrier thereof.

22. The compound of claim 1 wherein at least one of $R_1$, $R_2$, $R_3$, $R_4$, $R_5$, or $R_6$, is COOR, wherein said R is selected from the following counter-ions sodium, potassium, calcium, magnesium, ammonium, tromethamine and the like.

23. The compound of claim 1 wherein at least one of $R_1$, $R_2$, $R_3$, $R_4$, $R_5$, or $R_6$ is NR'R" wherein NR'R" represents a cyclic group selected from morpholine, piperidine, piperazine and the like.

24. The compound of claim 1 wherein at least one of $R_1$, $R_2$, $R_3$, $R_4$, $R_5$, or $R_6$ is $SO_3R'''$ wherein $R'''$ is selected from tetrazolyl, pyrrolyl, pyridyl, indolyl and the like.

25. The compound of claim 1 wherein two of $R_1$, $R_2$, $R_3$, $R_4$, $R_5$, or $R_6$ together represent a methylenedioxy or ethylenedioxy group.

26. The compound of claim 1 wherein two of $R_1$, $R_2$, $R_3$, $R_4$, $R_5$, or $R_6$ are present on adjacent carbon atoms and joined together to form a ring comprising a lactone or lactam group.

27. The compound of claim 1 wherein $A^-$ represents a counter ion selected from chloride, sulfate, phosphate, acetate and the like.

28. The compound of claim 1 wherein at least one of $R_1$, $R_2$, $R_3$, $R_4$, $R_5$ and $R_6$ is a chloroalkyl or a fluoroalkyl.

29. The compound of claim 1 wherein at least one of $R_1$, $R_2$, $R_3$, $R_4$, $R_5$ and $R_6$ is a trifluoromethoxy group or the like.

30. The compound of claim 1 wherein at $R_7$ is a chloroalkyl or a fluoroalkyl.

31. The compound of claim 1 wherein at $R_8$ is a chloroalkyl or a fluoroalkyl.

32. The compound of claim 1 wherein at least one of Y or Y' is a chloroalkyl or a fluoroalkyl.

33. The compound of claim 1 wherein $R_8$, is COOR, and R is selected from the following counter-ions: sodium, potassium, calcium, magnesium, ammonium, tromethamine and the like.

34. The compound of claim 1 wherein at least one of Y or Y', is COOR, and R is selected from the following counter-ions: sodium, potassium, calcium, magnesium, ammonium, tromethamine and the like.

35. The compound of claim 1 wherein at least one of Y or Y' is NR'R" and NR'R" represents a cyclic group selected from morpholine, piperidine, piperazine and the like.

36. The compound of claim 1 wherein Z is NR'R" and NR'R" represents a cyclic group selected from morpholine, piperidine, piperazine and the like.

37. The compound of claim 1 wherein at least one of Y or Y' is a trifluoromethoxy group or the like.

38. The compound of claim 1 wherein Z is a trifluoromethoxy group or the like.

39. The compound of claim 1 wherein $R_8$ is $SO_3R'''$ and $R'''$ is selected from tetrazolyl, imidazolyl, pyrrolyl, pyridyl, indoyl and the like.

40. The compound of claim 1 wherein at least one Y or Y' is $SO_3R'''$ and $R'''$ is selected from tetrazolyl, imidazolyl, pyrrolyl, pyridyl, indolyl and the like.

41. The compound of claim 1 wherein Y and Y' together are joined to form a ring selected from cyclopropyl, cyclobutyl, cyclopentyl, cyclohexyl and the like.

42. The compound of claim 1 wherein Y and Y' together are joined to form a ring comprising a heterocycle.

43. The compound of claim 42 wherein said heterocycle is a lactone or lactam.

* * * * *